US008765777B2

(12) United States Patent
Kalman et al.

(10) Patent No.: US 8,765,777 B2
(45) Date of Patent: Jul. 1, 2014

(54) COMPOSITIONS AND METHODS OF USE FOR TYROSINE KINASE INHIBITORS TO TREAT PATHOGENIC INFECTION

(75) Inventors: Daniel Kalman, Atlanta, GA (US); William Gerard Bornmann, Missouri City, TX (US); Patrick Michael Reeves, Atlanta, GA (US); Alyson Irene Swimm, Decatur, GA (US)

(73) Assignees: Emory University, Atlanta, GA (US); Sloan Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 12/969,659

(22) Filed: Dec. 16, 2010

(65) Prior Publication Data

US 2011/0281867 A1 Nov. 17, 2011

Related U.S. Application Data

(63) Continuation of application No. 12/774,828, filed on May 6, 2010, now abandoned, which is a continuation of application No. 12/551,871, filed on Sep. 1, 2009, now abandoned, which is a continuation of application No. 12/343,764, filed on Dec. 24, 2008, now abandoned.

(51) Int. Cl.
| | |
|---|---|
| *A61K 31/505* | (2006.01) |
| *A61K 31/506* | (2006.01) |
| *A61K 31/517* | (2006.01) |
| *A61K 31/496* | (2006.01) |
| *A61K 31/519* | (2006.01) |

(52) U.S. Cl.
CPC ............. *A61K 31/506* (2013.01); *A61K 31/517* (2013.01); *A61K 31/496* (2013.01); *A61K 31/519* (2013.01); *A61K 31/505* (2013.01)
USPC ........................................................ 514/275

(58) Field of Classification Search
CPC .. A61K 31/505; A61K 31/444; A61K 31/459
USPC ........................................................ 514/275
See application file for complete search history.

(56) References Cited

U.S. PATENT DOCUMENTS

| | | | |
|---|---|---|---|
| 4,439,089 A | 3/1984 | Anderson et al. |
| 5,521,184 A | 5/1996 | Zimmermann |
| 6,596,746 B1 | 7/2003 | Das et al. |
| 7,384,907 B2 | 6/2008 | Pendergast et al. |
| 2005/0003377 A1 | 1/2005 | Pendergast et al. |

FOREIGN PATENT DOCUMENTS

| | | |
|---|---|---|
| AU | 666709 | 10/1993 |
| AU | 2003276351 A1 | 4/2004 |
| EP | 0 564 409 A1 | 10/1993 |
| EP | 1 201 765 A2 | 5/2002 |

(Continued)

OTHER PUBLICATIONS

D. Leveque et al., "Clinical pharmacokinetics of imatinib mesylate," In Vivo 19:77-84, 2005.

(Continued)

*Primary Examiner* — San-Ming Hui
(74) *Attorney, Agent, or Firm* — Kilpatrick Townsend & Stockton, LLP

(57) ABSTRACT

Compositions and methods are provided for using tyrosine kinase inhibitors to treat pathogenic infection. In particular, methods for using Abl-family tyrosine kinase inhibitors to treat pathogenic infection are provided. Infections to be treated according to the present invention include, particularly, those caused by microbial pathogens such as bacteria and viruses.

18 Claims, 9 Drawing Sheets

(56) References Cited

FOREIGN PATENT DOCUMENTS

| | | |
|---|---|---|
| EP | 1 725 295 B1 | 11/2006 |
| JP | 06-87834 | 3/1994 |
| JP | H10509452 A | 9/1998 |
| JP | 2002-512962 | 8/2002 |
| JP | 2002-542193 | 10/2002 |
| JP | 2003-518077 | 3/2003 |
| WO | WO 96/15128 | 5/1996 |
| WO | WO 99/55335 | 11/1999 |
| WO | WO 00/62778 | 10/2000 |
| WO | WO 01/45751 | 6/2001 |
| WO | WO 02/10339 | 2/2002 |
| WO | WO 02/12238 | 2/2002 |
| WO | WO 02/24681 | 3/2002 |
| WO | WO 02/057240 | 7/2002 |
| WO | WO 02/057271 | 7/2002 |
| WO | WO 03/035049 | 5/2003 |
| WO | WO 03/035059 | 5/2003 |
| WO | WO 2004/026311 A2 | 4/2004 |
| WO | WO 2005/003325 | 1/2005 |
| WO | WO 2005/072826 | 8/2005 |
| WO | WO 2005/105097 | 11/2005 |
| WO | WO 2005/117885 | 12/2005 |
| WO | WO 2007/002441 | 1/2007 |
| WO | WO 2008/079460 | 7/2008 |

OTHER PUBLICATIONS

P. M. Reeves et al., "Variola and monkeypox viruses utilize conserved mechanisms of virion motility and release that depend on Abl and Src family tyrosine kinases," Journal Virology 85(1)21-31, Jan. 2011.

Anderson, P. (1995) "Mutagenesis," In; *C. elegans: Modern Biological Analysis of an Organism*, Epstein et al. eds., p. 31.

Barthold, S. W. (1980) "The microbiology of transmissible murine colonic hyperplasia," *Lab Anim Sci* 30:167.

Fenner, F.(1990) "Poxviruses," In; *Fields Virology*, Knipe, D.M. Ed., Raven Press: New York, pp. 2113-2133.

Fishman, J.A. (2002) "BK virus nephropathy—polyomavirus adding insult to injury," *N Engl J Med* 347(7):527-530.

Holmann et al. (1991) Epidemiology of progressive multifocal leukoencephalopathy in the United States: analysis of national mortality and AIDS surveillance data. *Neurology* 41:1733-1736.

McAllister et al. (2005) Functional genomics and the development of pathogenesis-therapies for Kaposi's sarcoma. *Pharmacogenomics* 6(3):235-44.

Morton et al. (1997) White, Effects of infusion rates in rats receiving repeated large volumes of saline solution intravenously. *Lab Anim Sci* 47(6):656-9.

Moss, B. (1990) Poxviridae: The Viruses and Their Replication, In; *Fields Virology*, Knipe, D.M. Ed., Raven Press: New York, p. 2079-2111.

Swedlow et al. (1997) Deconvolution in Optical Microscopy, in Deconvolution of Images and Spectra, P.A. Jansson, Editor. 1997, Academic Press, Inc.: San Diego. p. 284-309.

World Health Organization (2012) Tuberculosis. In *Fact Sheet*. World Health Organization, ed, Geneva, Switzerland.

Aderem et al. (1999) "Mechanisms of phagocytosis in macrophages," *Annu Rev Immunol* 17:593-623.

Agard et al. (1989) "Fluorescent Microscopy in Three Dimensions," *Methods Cell Biol*. 30:353.

Agosti et al. (2004) "Critical role for Kit-mediated Src kinase but not PI 3-kinase signaling in pro T and pro B cell development," *J Exp Med* 199(6):867-878.

Amorosa et al. (2003) "Separate worlds set to collide: smallpox, vaccinia virus vaccination, and human immunodeficiency virus and acquired immunodeficiency syndrome," *Clin Infect Dis* 37:426.

Anyanful et al. (2005) Paralysis and Killing of *Caenorhabditis elegans* by Enteropathogenic *Escherichia coli* Requires the Bacterial Tryptophanase Gene, *Molecular Microbiology* 57(4):968-1007.

Appay et al. (2002) "Memory CD8+ T cells vary in differentiation phenotype in different persistent virus infections," *Nat Med* 8(4):379-85.

Armstrong, J. (2000) How do Rab proteins function in membrane traffic, *Int J Biochem Cell Biol* 32(3):303-307.

Baas et al. (May 2, 2011) "Making the Most of the Hst," *SciBX* 4(19):A12-A15.

Bachmann et al. (2005) "Functional properties and lineage relationship of CD8+ T cell subsets identified by expression of IL-7 receptor alpha and CD62L," *J Immunol* 175(7):4686-96.

Backert (Feb. 2008) "Emerging Roles of Abl Family Tyrosine Kinases in Microbial Pathogenesis," *Trends Biochem Sci*. 33(2):80-90.

Badovinac et al. (2004 ) "CD8+ T cell contraction is controlled by early inflammation," *Nat Immunol* 5(8):809-817.

Badovinac et al. (2005) "Accelerated CD8+ T-cell memory and prime-boost response after dendritic-cell vaccination," *Nat Med* 11(7):748-756.

Barthold et al. (1978) "Transmissible murine colonic hyperplasia," *Vet Pathol* 15:223.

Barthold et al. (1977) "Dietary, bacterial, and host genetic interactions in the pathogenesis of transmissible murine colonic hyperplasia," *Lab Anim Sci* 27:938, Abstract only.

Baskaran et al. (1997) "Ataxia telangiectasia mutant protein activates c-Abl tyrosine kinase in response to ionizing radiation," *Nature* 387(6632):516-519.

Benjamin, T.L. (2001) "Polyoma virus: old findings and new challenges," *Virology* 289(2):167-173.

Berger et al. (2005) "Progressive multifocal leukoencephalopathy and natalizumab—unforeseen consequences," *N Engl J Med* 353(4):414-416.

Berger, J.R. (2003) "Progressive multifocal leukoencephalopathy in acquired immunodeficiency syndrome: explaining the high incidence and disproportionate frequency of the illness relative to other immunosuppressive conditions," *J Neurovirol*, 9(1):38-41.

Bettelheim et al. (2003) "Antibiotic resistance among verocytotoxigenic *Escherichia coli* (VTEC) and non-VTEC isolated from domestic animals and humans," *J Med Microbiol* 52:155.

Betts et al. (2003) "Sensitive and viable identification of antigen-specific CD8+ T cells by a flow cytometric assay for degranulation," *J Immunol Methods* 281(1-2):65-78.

Bishop et al. (2000) "Unnatural ligands for engineered proteins: new tools for chemical genetics," *Annu Rev Biophys Biomol Struct* 29:577.

Bishop, J.M. (1991) "Molecular themes in oncogenesis," *Cell* 64(2):235-248.

Bleed et al. (2000) "Dynamics and control of the global tuberculosis epidemic," *Curr Opin Pulm Med* 6(3):174-179.

Bommarius et al. (2007) "Enteropathogenic *Escherichia coli* Tir is an SH2/3 Ligand that Recruits and Activates Tyrosine Kinases Required for Pedestal Formation," *Molecular Miocrobiology* 63(6):1748-1768.

Boschelli et al. (1998) "Synthesis and Tyrosine Kinase Inhibitory Activity of a Series of 2-Amino-88-pyridoL2,3-dipyrimidines: Identification of Potent, Selective Platelet-Derived Growth Factor Receptor Tyrosine Kinase Inhibitors," *J. Med. CHem*. 41(22):4365-4377.

Bot et al. (Apr. 2002) "Genetic Immunization of Neonates," *Microbes Infect*. 4(4):511-520.

Bougneres et al. (2004) "Cortactin and Crk cooperate to trigger actin polymerization during Shigella invasion of epithelial cells," *J Cell Biol* 166(2):225-235.

Bronson et al. (1997) "Tumor induction by a transformation-defective polyoma virus mutant blocked in signaling through Shc," *Proc Natl Acad Sci U S A* 94(15): 7954-7958.

Buck et al. (2004) "A two-state allosteric model for autoinhibition rationalizes WASP signal integration and targeting," *J Mol Biol* 338(2):271-285.

Burgess et al. (2005) "Comparative analysis of two clinically active BCR-ABL kinase inhibitors reveals the role of conformation-specific binding in resistance," *Proc Natl Acad Sci U S A* 102(9):3395-3400.

Burton et al. (Oct. 2003) "Abl Tyrosine Kinases are Required for Infection by *Shigella flecneri*," *The EMBO J*. 22(20):5471-5479.

Cantwell et al. (1994) "Epidemiology of tuberculosis in the United States, 1985 through 1992," *Jama* 272(7):535-539.

Carson et al. (2003) "The Mre11 complex is required for ATM activation and the G2/M Checkpoint," *Embo J* 22(24):6610-6620.

(56) References Cited

OTHER PUBLICATIONS

Carter et al. (2003) "Vaccinia Viirus Cores are Transported on Microtubules," *J. Gen. Virol.* 84:2443-2458.
Cave et al. (1995) "Continuous intravenous infusion in the unrestrained rat—procedures and results," *Hum Exp Toxicol* 14(2):192-200.
Cebo et al. (2006) "The decreased susceptibility of Bcr/Abl targets to NK cell-mediated lysis in response to imatinib mesylate involves modulation of NKG2D ligands, GM1 expression, and synapse formation," *J Immunol* 176(2):864-872.
Chen et al. (2001) "CD8 T cells specific for human immunodeficiency virus, Epstein-Barr virus, and cytomegalovirus lack molecules for homing to lymphoid sites of infection," *Blood* 98(1):156-164.
Chen et al. (1999) "Radiation-induced assembly of Rad51 and Rad52 recombination complex requires ATM and c-Abl," *J Biol Chem* 274(18):12748-12752.
Clemens et al. (1995) "Characterization of the *Mycobacterium tuberculosis* phagosome and evidence that phagosomal maturation is inhibited," *J Exp Med* 181(1):257-270.
Clemens et al. (1996) "The *Mycobacterium tuberculosis* phagosome interacts with early endosomes and is accessible to exogenously administered transferrin," *J Exp Med* 184(4):1349-1355.
Cory et al. (2003) "Phosphorylation of the WASP-VCA domain increases its affinity for the Arp2/3 complex and enhances actin polymerization by WASP," *Mol Cell* 11(5):1229-1239.
Cory et al. (2002) "Phosphorylation of tyrosine 291 enhances the ability of WASp to stimulate actin polymerization and filopodium formation. Wiskott-Aldrich Syndrome protein," *J Biol Chem* 277(47):45115-45121.
Cowley et al. (2004) "The *Mycobacterium tuberculosis* protein serine/threonine kinase PknG is linked to cellular glutamate/glutamine levels and is important for growth in vivo," *Mol Microbiol* 52(6):1691-1702.
Coyne et al. (2006) "Virus-induced Abl and Fyn kinase signals permit coxsackievirus entry through epithelial tight junctions," *Cell* 124(1):119-131.
Cudmore et al. (1996) "Vaccinia Virus: A Model System for Actin-Membrane Interactions," *J. Cell. Sci.* 109(7):1739-1747.
Cudmore et al. (1997) "Viral manipulations of the actin cytoskeleton," *Trends Microbiol* 5(4):142-148.
Dahl et al. (1998) "Evidence of a role for phosphatidylinositol 3-kinase activation in the blocking of apoptosis by polyomavirus middle T antigen," *J. Virol.* 72:3221-3226.
Dahl et al. (2005) "Induction and utilization of an ATM signaling pathway by polyomavirus," *J Virol* 79(20):13007-13017.
De Stasio et al. (1997) "Characterization of revertants of unc-93(e1500) in *Caenorhabditis elegans* induced by N-ethyl-N-nitrosourea," *Genetics* 147:597.
Deng et al. (2004) "Dissecting virulence: systematic and functional analyses of a pathogenicity island," *Proc Natl Acad Sci U S A* 101:3597.
Desjardins, M. (1995) "Biogenesis of phagolysosomes: the 'kiss and run' hypothesis," *Trends Cell Biol* 5(5):183-186.
Di Taranto et al. (1997) "Detection of BK polyomavirus genotypes in healthy and HIV-positive children," *Eur J Epidemiol* 13(6):653-657.
Dilworth, S.M. (2002) "Polyoma virus middle T antigen and its role in identifying cancer-related molecules," *Nat. Rev. Cancer* 2:951-956.
Donaldson (Oct. 29, 2002) "Structure of a Regulatory Complex Involving the Abl SH3 Domain, the Crk SH2 Domain, and a Crk-Derived Phosphopeptide," *Proc. Nat. Acad. Sci. USA* 99(22):14053-14058.
Dorman et al. (1995) "The age-1 and daf-2 genes function in a common pathway to control the lifespan of *Caenorhabditis elegans*," *Genetics* 141:1399.
Dorsey et al. (Jan. 1, 2002) "Interleukin-3 Protects Bcr-Abl-Transformed Hematopoietic Progenitor Cells from Apoptosis Induced by Bcr-Abl Tyrosine Kinase Inhibitors," *Leukemia* 16(9):1589-1595.

Dorsey et al. (2000) "The pyrido[2,3-d]pyrimidine derivative PD180970 inhibits p210Bcr-Abl tyrosine kinase and induces apoptosis of K562 leukemic cells," *Cancer Res* 60:3127-3131.
Drake III et al. (1998) "β2-microglobulin knockout mice are highly susceptible to polyoma virus tumorigenesis," *Virology* 252:275-284.
Druker et al. (2002) "Chronic Myelogenous Leukemia," *Hematology* 2002:111-135.
Druker et al. (2001) "Chronic myelogenous leukemia," *Hematology* 2001:87-112.
Duménil et al. (Nov. 16, 1998) "Interferon α Inhibits a Src-Mediated Pathway Necessary for *Shigella*-Induced Cytoskeletal Rearrangements in Epithelial Cells," *J. Cell. Biol.* 143(4):1003-1012.
Dumenil et al. (2000) "Src tyrosine kinase activity down-regulates Rho-dependent responses during *Shigella* entry into epithelial cells and stress fibre formation," *J Cell Sci* 113(1):71-80.
Dye et al. (2002) "Worldwide incidence of multidrug-resistant tuberculosis," *J Infect Dis* 185(8):1197-1202.
Eash et al. (2004) "Infection of vero cells by BK virus is dependent on caveolae," *J Virol* 78(21):11583-11590.
Echarri et al. (2004) "Abl interactor 1 (Abi-1) wave-binding and SNARE domains regulate its nucleocytoplasmic shuttling, lamellipodium localization, and wave-1 levels," *Mol Cell Biol* 24(11):4979-4993.
Elwell et al. (2008) "RNA Interference Screen Identifies Abl Kinase and PDGFR Signaling in *Chlamydia trachomatisaeruginosa* Entry," *PLoS Pathog.* 4(3):e1000021.
Ernst, J.D. (1998) "Macrophage receptors for *Mycobacterium tuberculosis*," *Infect Immun* 66(4):1277-1281.
Esther et al. (Mar. 14, 1994) "Inhibition of Moloney Murine Leukemia Virus Replication bt Tyrophostins, Tyrosine Kinase Inhibitors," *FEBS Lett.* 341(1):99-103.
European Search Report, Application No. EP 10006351, Aug. 5, 2010, 3 pages.
European Search Report, Application No. EP 10006352, Oct. 7, 2010, 2 pages.
Evans et al. (2000) "Molecular approaches to receptors as targets for drug discovery," *Exs* 89:123-139, Abstract Only.
Farmer et al. (1998) "Community based approaches to the control of multidrug resistant tuberculosis: introducing "DOTS-plus"," *Bmj* 317(7159):671-674.
Feller, S.M. (2001) "Crk family adaptors-signalling complex formation and biological roles," *Oncogene* 20(44):6348-6371.
Ficarro et al. (2002) "Phosphoproteome analysis by mass spectrometry and its application to *Saccharomyces cerevisiae*," *Nat Biotechnol*, 20(3):301-305.
Finzi et al. (1999) "Latent infection of CD4+ T cells provides a mechanism for lifelong persistence of HIV-1, even in patients on effective combination therapy," *Nat Med* 5:512.
Fire et al. (1998) "Potent and specific genetic interference by double-stranded RNA in *Caenorhabditis elegans*," *Nature* 391:806.
Fratti et al. (2001) "Role of phosphatidylinositol 3-kinase and Rab5 effectors in phagosomal biogenesis and mycobacterial phagosome maturation arrest," *J Cell Biol*, 154(3):631-644.
Freund et al. (1992) "Polyoma virus middle T is essential for virus replication and persistence as well as for tumor induction in mice," *Virology* 191(2):716-723.
Frischknecht et al. (Jan. 1 2001) "Surfing Pathogens and the Lessions Learned for Actin Polymerization," *Trends Cell Biol*. 11(1):30-38.
Frischknecht et al. (1999) "Actin-based motility of vaccinia virus mimics receptor tyrosine kinase signalling" *Nature* 401(6756):926-929.
Fuller et al. (2005) "Cutting edge: emergence of CD127high functionally competent memory T cells is compromised by high viral loads and inadequate T cell help," *J Immunol* 174(10):5926-5930.
Garcea et al. (1989) "Separation of host range from transformation functions of the hr-t gene of polyomavirus," *Virology* 168: 312-319.
Garcia-Echeverria et al. (2000) "ATP site-directed competitive and irreversible inhibitors of protein kinases," *Med Res Rev* 20(1):28-57.
Garsin et al. (2003) "Long-lived *C. elegans* daf-2 mutants are resistant to bacterial pathogens," *Science* 300:1921.
Gee et al. (2006) "The role of sialic acid in human polyomavirus infections," *Glycoconj J* 23(1-2):19-26.

(56) References Cited

OTHER PUBLICATIONS

Gilbert et al. (2004) "Uptake pathway of polyomavirus via ganglioside GD1a," *J Virol*, 78(22): p. 12/259-67.

Gilbert et al. (2000) "Early steps of polyomavirus entry into cells," *J Virol* 74(18):8582-8588.

Gilbert et al. (2003) Cell penetration and trafficking of polyomavirus. *J Virol* 77(4):2615-22.

Goldman et al. (2001) Chronic myeloid leukemia: current treatment options. *Blood* 98(7):2039-42.

Goosney et al. (1999) Enteropathogenic *Escherichia coli* inhibits phagocytosis. *Infect Immun* 67:490.

Goosney et al. (2000) Gut feelings: enteropathogenic *E. coli* (EPEC) interactions with the host. *Annu Rev Cell Dev Biol* 16:173.

Gorska et al. (2004) Unc119, a novel activator of lck/fyn, is essential for T cell activation. *J Exp Med* 199:369.

Gottlieb et al. (2001) Natural biology of polyomavirus middle T antigen. *Microbiol Mol Biol Rev* 65(2):288-318.

Gould, I.M. (2002) Antibiotic policies and control of resistance. *Curr Opin Infect Dis* 15(4):395-400.

Gruenheid et al. (2001) Enteropathogenic *E. coli* Tir binds Nck to initiate actin pedestal formation in host cells. *Nat Cell Biol* 3:856-859.

Guinamard et al. (1998) Tyrosine phosphorylation of the Wiskott-Aldrich syndrome protein by Lyn and Btk is regulated by CDC42. *FEBS Lett* 434:431.

Gumireddy et al. (2005) A non-ATP-competitive inhibitor of BCR-ABL overrides imatinib resistance. *Proc Natl Acad Sci U S A* 102(6):1992-7.

Harrington et al. (2000) Differentiating between memory and effector CD8 T cells by altered expression of cell surface O-glycans. *J. Exp. Med.* 191:1241-1246.

Hatano et al. (2000) Pre-HAART HIV burden approximates post-HAART viral levels following interruption of therapy in patients with sustained viral suppression. *Aids* 14:1357.

Heinrich et al. (2000) Inhibition of c-kit receptor tyrosine kinase activity by STI 571, a selective tyrosine kinase inhibitor. *Blood* 96:925.

Hickson et al. (2004) Identification and characterization of a novel and specific inhibitor of the ataxia-telangiectasia mutated kinase ATM. *Cancer Res* 64(24):9152-9.

Hill et al. (2000) dpy-18 encodes an alpha-subunit of prolyl-4-hydroxylase in *Caenorhabditis elegans*. *Genetics* 155:1139.

Hirsch et al. (2005) The Src family kinase c-Yes is required for maturation of West Nile virus particles. *J Virol* 79(18):11943-51.

Hirsch et al. (2002) Prospective study of polyomavirus type BK replication and nephropathy in renal-transplant recipients. *N Engl J Med* 347(7):488-96.

Hollinshead et al. (2001) Vaccinia Virus Utilizes Microtubules for Movement to the Cell Surface, *J. Cell. Biol.* 154(2):389-402.

Hou, J. and E.O. Major, Progressive multifocal leukoencephalopathy: JC virus induced demyelination in the immune compromised host. *J Neurovirol* 6 Suppl 2:S98-S100, 2000.

Huang et al. (Dec. 12, 2002) "Inhibition of Bcr-Abl Kinase Activity by PD180970 Bocks Constitutive Activation of Stat5 Growth of CML Cells," *Oncogene* 21(57):8804-8816.

Hull, R.M., Guideline limit volumes for dosing animals in the preclinical stage of safety evaluation. Toxicology Subcommittee of the Association of the British Pharmaceutical Industry. *Hum Exp Toxicol* 14(3):305-7, 1995.

Huron et al. (2003) A novel pyridopyrimidine inhibitor of abl kinase is a picomolar inhibitor of Bcr-abl-driven K562 cells and is effective against STI571-resistant Bcr-abl mutants. *Clin Cancer Res* 9(4):1267-73.

International Search Report, International Application No. PCT/US2005/001710, Mailed Oct. 26, 2005, 4 pages.

Imperiale, M.J. (2000) The human polyomaviruses, BKV and JCV: molecular pathogenesis of acute disease and potential role in cancer. *Virology* 267:1-7.

Jerse et al. (1990) A genetic locus of enteropathogenic *Escherichia coli* necessary for the production of attaching and effacing lesions on tissue culture cells. *Proc Natl Acad Sci U S A* 87:7839.

Kaech et al. (2002) Effector and memory T-cell differentiation: implications for vaccine development. *Nat Rev Immunol* 2(4):251-62.

Kaech et al. (2003) Selective expression of the interleukin 7 receptor identifies effector CD8 T cells that give rise to long-lived memory cells. *Nat Immunol* 4(12):1191-8.

Kalman et al. (1999) Enteropathogenic *E. coli* acts through WASP and Arp2/3 complex to form actin pedestals. *Nat Cell Biol* 1(6):389-391.

Kemball et al. (2006) Costimulation requirements for antiviral CD8+ T cells differ for acute and persistent phases of polyoma virus infection. *J Immunol* 176(3):1814-24.

Kemball et al. (2005) Late priming and variability of epitope-specific CD8+ T cell responses during a persistent virus infection. *J Immunol.* 174(12):7950-60.

Kenny, B. (1999) "Phosphorylation of Tyrosine 474 of the Enteropathogenic *Escherichia coli* (EPEC) Tir Receptor Molecule is Essential for Actin Nucleating Activity and is Preceded by Additional Host Modifications," *Mol. Microbiol*. 31:1229-1241.

Kenny et al. (1997) Enteropathogenic *E. coli* (EPEC) transfers its receptor for intimate adherence into mammalian cells. *Cell* 91:511-520.

Kerkela et al. (2006) "Cardiotoxicity of the cancer therapeutic agent imatinib mesylate," *Nat Med* 12(8):908-916.

Kharbanda et al. (1997) Functional interaction between DNA-PK and c-Abl in response to DNA damage. *Nature* 386(6626):732-5.

Kieper et al. (1999) Homeostatic expansion and phenotypic conversion of naive T cells in response to self peptide/MHC ligands. *Proc Natl Acad Sci U S A* 96:13306.

Kim et al. (2006) Quantitative analysis of phosphotyrosine signaling networks triggered by CD3 and CD28 costimulation in Jurkat cells. *J Immunol* 176(5):2833-43.

Kim et al. (2005) Global phosphoproteome of HT-29 human colon adenocarcinoma cells. J Proteome Res 4(4):1339-1346.

Kim et al. (2001) A gene expression map for *Caenorhabditis elegans*. *Science* 293:2087-2092.

Klenerman et al. (2005) T cells and viral persistence: lessons from diverse infections. *Nat Immunol* 6(9):873-879.

Klutchko et al. (1998) "2-Substituted Aminopyrido[2,3-d]pyrimidin-7(sH)—ones. Structure-Activity Relationships Against Selected Tyrosine Kinases and in Vitro and in Vivo Anticancer Activity," *J. Med. Chem*. 41(17):3276-3292.

Knutton et al. (1989) "Diagnosis of enteropathogenic *Escherichia coli*," *Lancet* 2:218.

Koleske et al. (1998) Essential roles for the Abl and Arg tyrosine kinases in neurulation. *Neuron* 21(6):1259-72.

Kraker et al. (Oct. 1, 2000) "Biochemical and Cellular Effects of c-SRC Kinase-Selective Pyrido[2,3-*d*]pyrimidine Tyrosine Kinase Inhibitors," *Biochem Pharmacol*. 60(7):885-898.

Kudoh et al. (2005) Epstein-Barr virus lytic replication elicits ATM checkpoint signal transduction while providing an S-phase-like cellular environment. *J Biol Chem* 280(9):8156-63.

Kumar et al. (2007) Modeling HER2 Effects on Cell Behavior from Mass Spectrometry Phosphotyrosine Data. *PLoS Comput Biol* 3(1)e4:35-48.

Langhammer et al. (2011) "Inhibition of Poxvirus Spreading by the Anti-Tumor Drug Gefitinib (Iressa™)," *Antiviral Res*. 89:64-70.

Larsen et al. (2005) Highly selective enrichment of phosphorylated peptides from peptide mixtures using titanium dioxide microcolumns. *Mol Cell Proteomics* 4(7):873-886.

Lau et al. (2005) "Suppression of HIV-1 infection by a small molecule inhibitor of the ATM kinase," *Nat Cell Biol* 7(5):493-500.

Law et al. (Feb. 1, 2001) "Antibody Neutralization of the Extracellular Enceloped Form of Vaccinia Virus," *Virology* 280(1):132-142.

Law et al. (2002) Antibody-sensitive and antibody-resistant cell-to-cell spread by vaccinia virus: role of the A33R protein in antibody-resistant spread. *J Gen Virol* 83:209.

le Coutre et al. (2004) Pharmacokinetics and cellular uptake of imatinib and its main metabolite CGP74588. *Cancer Chemother Pharmacol* 53:313-23.

(56) References Cited

OTHER PUBLICATIONS

Lebeis et al. (Feb. 19, 2009) "Aligning Antimicrobial Drug Discovery with Complex and Redundant Host-Pathogen Interactions," *Cell Host & Microb.* 5:1-9.

Lee et al. (2004) "Cutaneous Side Effects in Non-Small Cell Lung Cancer Patients Treated with Iressa (ZD1839), an Inhibitor of Epidermal Growth Factor," *Acta. Derm. Venereol.* 84(1):23-26.

Lee et al. (2006) "A mouse model for polyomavirus-associated nephropathy of kidney transplants," *Am J Transplant* 6(5):913-922.

Li et al. (2004) p150(Sal2) is a p53-independent regulator of p21(WAF1/CIP). *Mol Cell Biol* 24(9):3885-93.

Liang (Aug. 2005) "*cis*-Acting Packaging Signals in the Influenza Virus PB1, PB2, and PA Genomic RNA Segments," *J. Virol.* 79(16):10348-10355.

Liebl et al. (2006) Mouse Polyomavirus Enters Early Endosomes, Requires Their Acidic pH for Productive Infection, and Meets Transferrin Cargo in Rab11-Positive Endosomes. *J Virol* 80(9):4610-22.

Lilley et al. (2005) DNA repair proteins affect the lifecycle of herpes simplex virus 1. *Proc Natl Acad Sci U S A* 102(16):5844-9.

Liu et al. (1999) "Structural basis for selective inhibition of Src family kinases by PP1," *Chem Biol* 6:671-679.

Liu et al. (1998) A molecular gate which controls unnatural ATP analogue recognition by the tyrosine kinase v-Src. *Bioorg Med Chem* 6:1219.

Liu et al. (1998) Engineering Src family protein kinases with unnatural nucleotide specificity. *Chem Biol* 5:91.

Liu et al. (2000) Src-Abl tyrosine kinase chimeras: replacement of the adenine binding pocket of c-Abl with v-Src to swap nucleotide and inhibitor specificities. *Biochemistry* 39:14400.

Lommel et al. (2001) Actin pedestal formation by enteropathogenic *Escherichia coli* and intracellular motility of *Shigella flexneri* are abolished in N-WASP-defective cells. *EMBO Rep* 2:850-857.

Longnecker et al. (1991) An Epstein-Barr virus protein associated with cell growth transformation interacts with a tyrosine kinase. *J Virol* 65:3681.

Lukacher et al. (1999) Visualization of polyoma virus-specific CD8+ T cells in vivo during infection and tumor rejection. *J Immunol* 163(6):3369-78.

Lukacher et al. (1993) PyvS: a dominantly acting gene in C3H/BiDa mice conferring susceptibility to tumor induction by polyoma virus. *Virology* 196(1):241-8.

Lukacher et al. (1995) Susceptibility to tumors induced by polyoma virus is conferred by an endogenous mouse mammary tumor virus superantigen. *J. Exp. Med.* 181:1683-1692.

Lupberger et al. (May 2011) "EGFR and EphA2 are Host Factors for Hepatitis C Virus Entry and Possible Targets for Antiviral Therapy," *Nature Med.* 17(5):589-595.

Luperchio et al. (2001) Molecular pathogenesis of *Citrobacter rodentium* and transmissible murine colonic hyperplasia. *Microbes Infect* 3:333.

Ly et al. (2009) Abelson Tyrosine Kinase Facilitates *Salmonella enterica* serovar Typhimurium Entry into Epithelial Cells. *Infect Immun* 77(1):60.

March et al. (1989) Serotonin and treatment in obsessive-compulsive disorder, *Psychiatric Developments* 7(1):1-18, Abstract Only.

Marsh et al. (2006) Virus entry: open sesame. *Cell* 124(4):729-40.

Mattiuzzi et al. (2003) "Development of Varicella-Zoster virus infection in patients with chronic myelogenous leukemia treated with imatinib mesylate," *Clin Cancer Res* 9(3): 976-980.

Mayer et al. (1994) Mutagenic analysis of the roles of SH2 and SH3 domains in regulation of the Abl tyrosine kinase. *Mol Cell Biol* 14:2883.

McDaniel et al. (1997) A cloned pathogenicity island from enteropathogenic *Escherichia coli* confers the attaching and effacing phenotype on *E. coli* K-12. *Mol Microbiol* 23:399.

McDaniel et al. (1995) A genetic locus of enterocyte effacement conserved among diverse enterobacterial pathogens. *Proc Natl Acad Sci U S A* 92:1664.

McFadden, G. (Jul. 2005) "Gleevec Casts a Pox on Poxviruses," *Nat. Med.* 11(7):711-712.

McMillen et al. (1977) Immunological reactivity of antisera to sodium dodecyl sulfate-derived polypeptides of polyoma virions. *J Virol* 21(3):1113-20.

Mello et al. (1995) DNA Transformation. Chapter 19, In *C. elegans: Modern Biological Analysis of an Organism*. H. Epstein, and D. Shakes, eds, pp. 451-482.

Messerschmitt et al. (1997) DNA tumor viruses and Src family tyrosine kinases, an intimate relationship. *Virology* 227:271.

Miller et al. (2001) Identification of two *Mycobacterium tuberculosis* H37Rv ORFs involved in resistance to killing by human macrophages. *BMC Microbiol* 1:26.

Moreau et al. (2000) A complex of N-WASP and WIP integrates signalling cascades that lead to actin polymerization, *Nat. Cell Biol.* 2:441-448.

Morton et al. (1997) Histologic lesions associated with intravenous infusions of large volumes of isotonic saline solution in rats for 30 days. *Toxicol Pathol* 25(4):390-4.

Moses et al. (2002) "Kaposi's sarcoma-associated herpesvirus-induced upregulation of the c-kit proto-oncogene, as identified by gene expression profiling, is essential for the transformation of endothelial cells," *J Virol* 76(16):8383-8399.

Murphy et al. (2003) Genes that act downstream of DAF-16 to influence the lifespan of *Caenorhabditis elegans*. *Nature* 424:277.

Nagar et al. (2002) Crystal Structures of the Kinase Domain of c-Abl in Complex with the Small Molecule Inhibitors PD173955 and Imatinib (STI-571). *Cancer Res* 62(15):4236-43.

Napier et al. (Nov. 2011) Imatinib-Sensitive Tyrosine Kinases Regulate Mycobacterial Pathogenesis and Represent Therapeutic Targets against Tuberculosis, *Cell Host & Microbe* 10:475-485.

Neumann (Aug. 1999) "Generation of Influenza A Viruses Entirely from Cloned cDNAs," *Proc. Nat. Acad. Sci. USA* 96:9345-9350.

Newsome et al. (2004) "SRC mediates a switch from microtubule- to actin-based motility of vaccinia virus," *Science* 306(5693):124-129.

O'Brien et al. (1996) In vitro interaction of *Mycobacterium tuberculosis* and macrophages: activation of anti-mycobacterial activity of macrophages and mechanisms of anti-mycobacterial activity. *Current Topics in Microbiology & Immunology* 215:97, Abstract Only.

O'Hare et al. (2005) "In vitro activity of Bcr-Abl inhibitors AMN107 and BMS-354825 against clinically relevant imatinib-resistant Abl kinase domain mutants," *Cancer Res* 65(11):4500-4505.

O'Hare et al. (2005) *AMN107: tightening the grip of imatinib. Cancer Cell* 7(2):117-9.

Pallas et al. (1986) Polyomavirus small t antigen: overproduction in bacteria, purification, and utilization for monoclonal and polyclonal antibody production. *J Virol* 60(3):1075-84.

Pantaleo et al. (2006) Functional signatures in antiviral T-cell immunity for monitoring virusassociated diseases. *Nat Rev Immunol* 6(5):417-23.

Parkinson et al. (1994) Vaccinia virus gene A36R encodes a M(r) 43-50 K protein on the surface of extracellular enveloped virus. *Virology* 204:376-390.

Pelkmans et al. (2002) Local actin polymerization and dynamin recruitment in SV40-induced internalization of caveolae. *Science* 296(5567):535-9.

Pelkmans et al. (2001) Caveolar endocytosis of simian virus 40 reveals a new two-step vesicular-transport pathway to the ER. *Nat Cell Biol* 3(5):473-83.

Pelkmans, L. (2005) Viruses as probes for systems analysis of cellular signalling, cytoskeleton reorganization and endocytosis. *Curr Opin Microbiol* 8(3):331-337.

Perna et al. (Jan. 25, 2001) "Genome Sequence of Enterohaemorrhagic *Escherichia coil* O157:H7," *Nature* 409(6819):529-533.

Perna et al. (1998) Molecular evolution of a pathogenicity island from enterohemorrhagic *Escherichia coli* O157:H7. *Infect Immun* 66:3810.

Peroutka et al. (Summer 1989) "The Clinical Utility of Pharmacological Agents that Act at Serotonin Receptors," *J. Neuropsy. Clin. Neurosci.* 1(3):253-262.

Pielage et al. (2008) "RNAi Screen Reveals an Abl Kinase-Dependent Host Cell Pathway Involved in *Pseudomonas aeruginosa* Internalization," *PloS Pathog* 4(3):e1000031.

(56) References Cited

OTHER PUBLICATIONS

Ploubidou et al. (2000) "Vaccinia Virus Infection Disrupts Microtubule Organization and Centrosome Function," *EMBO J.* 19(15):3932-3944.
Pluk et al. (Jan. 25, 2002) "Autoinhibition of c-Abl," *Cell* 108:247-259.
Poppe et al. (2007) Phosphorylation of Helicobacter pylori CagA by c-Abl leads to cell motility. *Oncogene* 26(24):3462-72.
Qie et al. (Apr. 10, 1999) "Herpes Simplex Virus Entry is Associated with Tyrosine Phosphorylation of Cellular Proteins," *Virology* 256(2):220-227.
Querbes et al. (2004) A JC virus-induced signal is required for infection of glial cells by a clathrin- and eps15-dependent pathway. *J Virol* 78(1):250-6.
Ragno et al. (2001) Changes in gene expression in macrophages infected with *Mycobacterium tuberculosis*: a combined transcriptomic and proteomic approach. *Immunology* 104(1):99-108.
Ramirez et al. (2003) "Tissue Distribution of the Ankara Strain of Vaccinia Virus (MVA) after Mucosal or Systemic Administration," *Arch. Virol.* 148(5):827-839.
Raptis et al. (1985) Regulation of cellular phenotype and expression of polyomavirus middle T antigen in rat fibroblasts. *Mol. Cell. Biol.* 5:2476-2485.
Raviglione et al. (1995) Global epidemiology of tuberculosis. Morbidity and mortality of a worldwide epidemic. *Jama* 273(3):220-6.
Reading et al. (2003) "A Soluble Chemokine-Binding Protein from Vaccinia Virus Reduces Virus Virulence and the Inflammatory Response to Infection," *J. Immunol.* 170:1435-1442.
Reeves et al. (2005) "Disabling poxvirus pathogenesis by inhibition of Abl-family tyrosine kinases," *Nat Med* 11(7):731-739.
Reeves et al. (Jan. 2011) "Variola and Monkeypox Viruses Utilize Conserved Mechanisms of Virion Motility and Release that Depend on Abl and Src Family Tyrosine Kinases," *J. Birol.* 85(1):21-31.
Rempel et al. (Jul. 1992) "Vaccinia Virus B1 Kinase: Phenotypic Analysis of Temperature-Sensitive Mutants and Enzymatic Characterization of Recombinant Proteins," *J. Virol.* 66(7):4413-4426.
Rietdorf et al. (2001) "Kinesin-Dependent Movement on Microtubules Preceded Actin-Based Motility of Vaccinia Virus," *Nat. Cell Biol.* 3(11):992-1000.
Roberts et al. (2005) Differential contributions of central and effector memory T cells to recall responses. *J Exp Med* 202(1):123-33.
Rohatgi et al. (Apr. 16, 1999) "The Interaction Between N-WASP and the Arp2/3 Complex Links Cdc42-Dependent Signals to Actin Assembly," *Cell* 97:221-231.
Rohde et al. (2007) *Mycobacterium tuberculosis* invasion of macrophages: linking bacterial gene expression to environmental cues. *Cell Host Microbe* 2(5):352-64.
Ross et al. (2004) "Multiplexed protein quantitation in *Saccharomyces cerevisiae* using amine-reactive isobaric tagging reagents," *Mol Cell Proteomics* 3(12):1154-1169.
Russell, D. G. (2001) *Mycobacterium tuberculosis*: here today, and here tomorrow. *Nat Rev Mol Cell Biol* 2:569.
Russell et al. (1997) Why intracellular parasitism need not be a degrading experience for *Mycobacterium*. *Philosophical Transactions of the Royal Society of London-Series B: Biological Sciences* 352:1303.
Russell et al. (2002) *Mycobacterium* and the coat of many lipids. *J Cell Biol* 158(3):421-6.
Russell et al. (1996) *Mycobacterium avium*- and *Mycobacterium tuberculosis*-containing vacuoles are dynamic, fusion-competent vesicles that are accessible to glycosphingolipids from the host cell plasmalemma. *J Immunol* 156(12):4764-73.
Sallusto et al. (1999) Two subsets of memory T lymphocytes with distinct homing potentials and effector functions. *Nature* 401:708-712.
Salomon et al. (2003) "Profiling of tyrosine phosphorylation pathways in human cells using mass spectrometry," *Proc Natl Acad Sci U S A* 100(2):443-448.
Sampson et al. (2003) Bacterial genomics and vaccine design. *Expert Rev Vaccines* 2(3):437-45.

Scaplehorn et al. (Apr. 30, 2002) "Grb2 and Nck Act Cooperatively to Promote Actin-Based Motility of Vaccinia Virus," *Curr. Biol.* 12:740-745.
Schindler et al. (2000) Structural mechanism for STI-571 inhibition of abelson tyrosine kinase. *Science* 289(5486):1938-42.
Schlesinger et al. (1990) Phagocytosis of *Mycobacterium tuberculosis* is mediated by human monocyte complement receptors and complement component C3. *J Immunol* 144(7):2771-80.
Schmelzle et al. (2006) Phosphoproteomic approaches to elucidate cellular signaling networks. *Curr Opin Biotechnol* 17(4):406-14.
Schmelzle et al. (2006) Temporal dynamics of tyrosine phosphorylation in insulin signaling. *Diabetes* 55(8):2171-9.
Schwartzberg et al. (1991) Mice homozygous for the ablm1 mutation show poor viability and depletion of selected B and T cell populations. *Cell* 65(7):1165-75.
Selbach et al. (Mar. 1, 2002) "Src is the Kinase of the *Heliobacter pylori* CagA Protein In Vitro and In Vivo," *J. Biol. Chem.* 277(9):6775-6778.
Shah et al. (1997) Engineering unnatural nucleotide specificity for Rous sarcoma virus tyrosine kinase to uniquely label its direct substrates. *Proc Natl Acad Sci U S A* 94:3565.
Shah et al. (2004) Overriding imatinib resistance with a novel ABL kinase inhibitor. *Science* 305(5682):399-401.
Shaw et al. (2002) Enteropathogenic *Escherichia coli* translocate Tir and form an intimin-Tir intimate attachment to red blood cell membranes. *Microbiology* 148:1355.
Shim, J.L. (1972) "The Synthesis of Pyrido[2,3-d]pyrimidine Derivatives as Potential Antitumor and Antibacterial Agents," *Dissertation Abstracts Int. B* 33(3):1063-1064.
Simmons et al. (2002) "Impaired resistance and enhanced pathology during infection with a noninvasive, attaching-effacing enteric bacterial pathogen, *Citrobacter rodentium*, in mice lacking IL-12 or IFN-gamma," *J Immunol* 168:1804.
Smith et al. (Dec. 2002) "The Formation and Function of Extracellular Enveloped Vaccinia Virus," *J. Gen. Virol.* 83(12):2915-2931.
Smith et al. (2003) "Emerging Roles of Targeted Small Molecule Protein-Tyrosine Kinase Inhibitors in Cancer Therapy," *Oncol. Res.* 14(4-5):175-225.
Smith et al. (Oct. 2003) "Vaccinia Virus Motility," *Ann. Rev. Microbiol.* 57:323-342.
Smith et al. (2004) How viruses enter animal cells. *Science* 304(5668):237-242.
Stamm et al. (2005) Role of the WASP family proteins for *Mycobacterium marinum* actin tail formation. *Proc Natl Acad Sci U S A* 102(41):14837-42.
Stein et al. (2002) c-Src/Lyn kinases activate *Helicobacter pylori* CagA through tyrosine phosphorylation of the EPIYA motifs. *Mol Microbiol* 43(4):971-80.
Stolt (2003) Seroepidemiology of the human polyomaviruses. *J. Gen. Virol.* 84:1499-1504.
Stradal et al. (2001) The Abl interactor proteins localize to sites of actin polymerization at the tips of lamellipodia and filopodia. *Curr Biol* 11(11):891-5.
Sturgill-Koszycki et al. (1986) *Mycobacterium*-containing phagosomes are accessible to early endosomes and reflect a transitional state in normal phagosome biogenesis. *Embo J* 15(24):6960-8.
Sullivan et al. (2003) Antigen-driven effector CD8 T cell function regulated by T-bet. *Proc Natl Acad Sci U S A* 100:15818.
Sumen et al. (2004) Intravital microscopy: visualizing immunity in context. *Immunity* 21(3):315-29.
Swimm et al. (Aug. 2004) "Enteropathogenic *Escherichia coli* use redundant tyrosine kinases to form actin pedestals," *Mol. Biol. Cell.* 15(8):3520-3529.
Swimm et al. (May 2010) "Abl Family Tyrosine Kinases Regulate Sialyated Ganglioside Receptors for Polyomavirus," *J. Virol.* 84(9):4243-4251.
Tammer et al. (2007) Activation of Abl by *Helicobacter pylori*: a novel kinase for CagA and crucial mediator of host cell scattering. *Gastroenterology* 132(4):1309-19.
Tang et al. (Apr. 1994) "*Listeria Monocytogenes*, an Invasive Bacterium, Stimulates MAP Kinase Upon Attachment to Epithelial Cells," *Mol. Biol. Cell.* 5(4):455-464.

(56) References Cited

OTHER PUBLICATIONS

Tanis et al. (Jun. 2003) Two Distinct Phosphorylation Pathways Have Additive Effects on Abl Family Kinase Activation, *Mol. Cell. Biol.* 23(11):3884-3896.
Tatton et al. (Feb. 14, 2003) "The Src-Selective Kinase Inhibitor PP1 Also Inhibits Kit and Bcr-Abl Tyrosine Kinases," *J. Biol. Chem.* 278(7):4847-4853.
Taube et al. (2004) Mast Cells, FceRI, and IL-13 Are Required for Development of Airway Hyperresponsiveness after Aerosolized Allergen Exposure in the Absence of Adjuvant, *J Immunol* 172:6398-6406.
Taunton et al. (2000) "Actin-dependent propulsion of endosomes and lysosomes by recruitment of N-WASP," *J Cell Biol* 148(3):519-530.
Tian et al. (2004) Identification of TAZ as a binding partner of the polyomavirus T antigens. *J Virol* 78(22):12657-64.
Tobin et al. (2008) Comparative pathogenesis of *Mycobacterium marinum* and *Mycobacterium tuberculosis*. *Cell Microbiol* 10(5):1027-39.
Torres et al. (2003) Contingent phosphorylation/dephosphorylation provides a mechanism of molecular memory in WASP. *Mol Cell* 11(5):1215-27.
Traktman et al. (Dec. 25, 1989) "Vaccinia Virus Encodes an Essential Gene with Strong Homology to Protein Kinases," *J. Biol. Chem.* 264(36):21458-21561.
Traktman et al. (Oct. 1995) "Temperature—Sensitive Mutants with Lesions in the Vaccinia Virus F10 Kinase Undergo Arrest at the Earliest Stage of Virion Morphogenesis," *J. Virol.* 69(10):6581-6587.
Tscharke et al. (1999) A model for vaccinia virus pathogenesis and immunity based on intradermal injection of mouse ear pinnae. *J Gen Virol* 80 (Pt 10):2751-2755.
Tscharke et al. (2002) Dermal infection with vaccinia virus reveals roles for virus proteins not seen using other inoculation routes. *J Gen Virol* 83:1977-1986.
Vallance et al. (2002) Mice lacking T and B lymphocytes develop transient colitis and crypt hyperplasia yet suffer impaired bacterial clearance during *Citrobacter rodentium* infection. *Infect Immun* 70:2070.
Van Doorn et al. (Sep. 2002) "Follicular and Epidermal Alterations n Patients Treated with ZD1839 (Iressa), and Inhibitor of the Epidermal Growth Factor Receptor," *Br. J. Dermatol.* 147(3):598-601.
van Kessel et al. (2008) Efficient point mutagenesis in mycobacteria using single-stranded DNA recombineering: characterization of antimycobacterial drug targets. *Mol Microbiol*, 2008. 67(5):1094-1107.
van Kessel et al. (2008) Mycobacterial recombineering. *Methods Mol Biol* 435:203-215.
van Kessel et al. (2007) Recombineering in *Mycobacterium tuberculosis*. *Nat Methods* 4(2):147-52.
van Kessel et al. (2008) Recombineering mycobacteria and their phages. *Nat Rev Microbiol* 6(11):851-7.
Vanichkin et al. (1996) "Late Administration of a Lipophilic Tyrosine Kinase Inhibitor Prevents Lipopolysaccharide and *Escherichia coli*-Induced Lethal Toxicity," *J. Infect. Dis.* 173:927-933.
Varga et al. (2001) Independent regulation of lymphocytic choriomeningitis virus-specific T cell memory pools: relative stability of CD4 memory under conditions of CD8 memory T cell loss. *J Immunol* 166:1554.
Vergne et al. (2005) Mechanism of phagolysosome biogenesis block by viable *Mycobacterium tuberculosis*. *Proc Natl Acad Sci U S A* 102(11):4033-8.

Wang et al. (2005) Imatinib mesylate (STI-571) enhances antigen-presenting cell function and overcomes tumor-induced CD4+ T-cell tolerance. *Blood* 105(3):1135-43.
Wang, J.Y. (2000) Regulation of cell death by the Abl tyrosine kinase. *Oncogene* 19(49):5643-50.
Ward et al. (May 2001) "Visulaization of Intracellulat Movement of Vaccinia Virus Virions Containing a Green Fluorescent Protein-B5R Membrane Protein Chimera," *J. Virol.* 75(10):4802-4813.
Ward et al. (Dec. 2001) "Vaccina Virus Intracellulat Movement is Associated with Microtubules and Independent of Actin Tails," *J. Virol.* 75(23):11651-11663.
Ward et al. (2003) Mapping and functional analysis of interaction sites within the cytoplasmic domains of the vaccinia virus A33R and A36R envelope proteins. *J Virol* 77:4113.
Wei et al. (Apr. 2005) "Mast Cells Limit Systemic Bacterial Dissemination but not Colitis in Response to *Citrobacter rodentium*," *Infect. Immun.* 73(4):1978-1985.
Weisberg et al. (2005) "Characterization of AMN107, a selective inhibitor of native and mutant Bcr-Abl," *Cancer Cell* 7(2):129-141.
Welch et al. (1993) A C-terminal protein-binding domain in the retinoblastoma protein regulates nuclear c-Abl tyrosine kinase in the cell cycle. *Cell* 75:779.
Welsh, R. M. (2001) Assessing CD8 T cell number and dysfunction in the presence of antigen. *J Exp Med* 193:F19.
Wherry et al. (2004) Memory CD8 T-cell differentiation during viral infection. *J Virol* 78(11):5535-45.
Wherry et al. (2004) Antigen-independent memory CD8 T cells do not develop during chronic viral infection. *Proc Natl Acad Sci U S A* 101(45):16004-9.
Wherry et al. (2003) Viral persistencealters CD8 T-cell immunodominance and tissue distribution and results in distinct stages of functional impairment. *J Virol* 77(8):4911-27.
Wherry et al. (2003) Lineage relationship and protective immunity of memory CD8 T cell subsets. *Nat Immunol* 4(3):225-34.
Williams et al. (2005) "Leflunomide for polyomavirus type BK nephropathy," *N Engl J Med* 352(11):1157-1158.
Wisniewski et al. (2002) "Characterization of potent inhibitors of the Bcr-Abl and the c-kit receptor tyrosine kinases," *Cancer Res* 62(15):4244-4255.
Witucki et al. (2002) Mutant tyrosine kinases with unnatural nucleotide specificity retain the structure and phospho-acceptor specificity of the wild-type enzyme. *Chem Biol* 9:25.
Wolff et al. (2001) Establishment of a murine model for therapy-treated chronic myelogenous leukemia using the tyrosine kinase inhibitor ST1571. *Blood* 98:2808.
Wolffe et al. (1998) Role for the vaccinia virus A36R outer envelope protein in the formation of virus-tipped actin-containing microvilli and cell-to-cell virus spread. *Virology* 244:20-26.
Woodring et al. (2001) Inhibition of c-Abl tyrosine kinase activity by filamentous actin. *J Biol Chem* 276:27104.
Yuwen et al. (1993) Nuclear localization of a double-stranded RNA-binding protein encoded by the vaccinia virus E3L gene, *Virology* 195:732-744.
Zhang et al. (2007) Quantitative proteomic analysis of phosphotyrosine-mediated cellular signaling networks. *Methods Mol Biol* 359:203-12.
Zhang et al. (2005) Time-resolved mass spectrometry of tyrosine phosphorylation sites in the epidermal growth factor receptor signaling network reveals dynamic modules. *Mol Cell Proteomics* 4(9):1240-50.
Zimmerli et al (1996) Selective receptor blockade during phagocytosis does not alter the survival and growth of *Mycobacterium tuberculosis* in human macrophages. *Am J Respir Cell Mol Biol* 15:760-770.

A.

B.

pretreatment reversal

COMPOSITIONS AND METHODS OF USE FOR TYROSINE KINASE INHIBITORS TO TREAT PATHOGENIC INFECTION

CROSS-REFERENCE TO RELATED APPLICATIONS

This application is a continuation of U.S. application Ser. No. 12/774,828, filed May 6, 2010, which is a continuation of U.S. application Ser. No. 12/551,871, filed Sep. 1, 2009, which is a continuation of U.S. application Ser. No. 12/343,764, filed Dec. 24, 2008, which is a continuation of U.S. application Ser. No. 10/586,382, filed Jul. 19, 2006, which is a U.S. National Stage of International Application No. PCT/US2005/001710, filed Jan. 20, 2005, which claims the benefit of U.S. Application No. 60/537,960, filed Jan. 21, 2004, U.S. Application No. 60/553,681, filed Mar. 16, 2004, and U.S. Application No. 60/614,203, filed Sep. 29, 2004; all of which are hereby incorporated by reference to the extent not inconsistent with the disclosure herewith.

STATEMENT REGARDING FEDERALLY SPONSORED RESEARCH OR DEVELOPMENT

This invention was made with government support under AI056067 awarded by the National Institutes of Health. The United States Government has certain rights in the invention.

FIELD OF THE INVENTION

The invention relates to compositions and methods for using tyrosine kinase inhibitors to treat pathogenic infection associated with or caused by host-cell interactions involving tyrosine kinases. In particular, the present invention relates to the use of Abl-family tyrosine kinase inhibitors to treat infection from microbial pathogens such as bacteria and viruses.

BACKGROUND OF THE INVENTION

The last several decades have witnessed an onslaught of deadly pathogens around the globe. A broad array of human pathogens exists, including various microbes such as bacteria, protozoa, viruses, algae, and fungi. The innate capacity to respond to selective pressures has driven the evolution of microbes and enabled them to adapt to complex and variable environments. It is perhaps no surprise, then, that infectious microbes have readily evolved mechanisms to evade our attempts to destroy them with synthetic or natural anti-microbial compounds.

The fact that microbes develop resistance at a rate that far exceeds development of new therapeutics arguably poses the single most serious public health threat in this century in both developing and developed nations. There is no denying that anti-microbial strategies have met with spectacular success over the last century. For example, antibacterial and antiviral drugs directed at targets within the pathogen have been used to save countless lives. But it is becoming increasingly evident that such success is not sustainable. To counter these drugs, bacteria and viral pathogens have evolved sophisticated mechanisms to inactivate these compounds. Examples include the pan-drug resistant strains of *Staphylococcus aureus, Klebsiella pneumonia*, and *Pseudomonas aerginosa*, and *Mycobacterium tuberculosis* (TB) among bacteria and human immunodeficiency virus (HIV) among viruses.

More worrisome still is the lack of effort on the part of pharmaceutical companies (big or small) to pursue development of new antimicrobials. Efforts to develop new antibiotics by the pharmaceutical industry by large-scale screens of chemical libraries that inhibit growth have largely failed, and new tetracycline and sulfanilamide analogs will likely engender resistance and will quickly be rendered useless. The resistance problem is compounded further by indiscriminate and inappropriate use of antibiotics and antiviral compounds without compliance measures or public health policies to reduce disease burden. With the astounding costs of clinical trials (e.g., approximately $400M to bring new tetracyclines to the market for an expected revenue of $100M), the failure to control generic sales, and the capacity to generate substantial revenues from medications for chronic illnesses there is little if any financial incentive for big pharmaceutical companies to even develop new antibiotics, and small biotechnology companies simply do not have the resources.

Even with the current level of effort there is cause for concern. Of the new drugs under development, most, if not all, will likely engender resistance quickly upon release (e.g., folate biosynthesis inhibitor Icalprim). The search for novel antiviral compounds has been somewhat more successful and largely motivated by the HIV pandemic, but drugs have been developed principally against viral targets, and mutation rates among viruses still outpaces new development. One positive development has been vaccines, which are promising for some bacterial and viral illnesses. But vaccines are not successful in all cases (e.g., in young children), and adequate resources have not been made available.

There is therefore an urgent need to develop compounds and methods effective for the prevention and treatment of pathogenic infection.

SUMMARY OF THE INVENTION

Compositions and methods for treating pathogenic infection are provided. Compositions of the invention comprise compounds that inhibit tyrosine kinases involved in pathogen-host cell interactions that are associated with or cause pathogenic infection. In some embodiments, the invention relates to the use of inhibitors of Ableson (Abl) family tyrosine kinase inhibitors such as imatinib mesylate, pyrido [2,3-d]pyrimidines, or pharmaceutically acceptable salts, enantiomers, analogs, esters, amides, prodrugs, metabolites, or derivatives thereof.

The methods of the invention comprise administering the compositions described above in therapeutically effective amounts to a patient in need thereof for treating infection by a broad array of pathogens, including microbial pathogens such as bacteria, protozoa, viruses, algae, and fungi. In particular, the invention relates to the use of these compositions to treat disease associated with bacterial and viral pathogens including pathogenic *Escherichia coli* (enteropathogenic *Escherichia coli* (EPEC), enterohemmorhagic *Escherichia coli* (EHEC), uropathogenic *Escherichia coli* (UPEC), and enteroinvasive *Escherichia coli* (EIEC)), *Helicobacter pylori, Listeria monocytogenes, Salmonella typhimurium, Shigella flexneri, Mycobacterium tuberculosis* (mTB), Pox viruses (including Vaccinia and variola viruses), polyoma viruses (including JC and BK viruses), Herpes viruses, cytomegalovirus (CMV), and human immunodeficiency viruses (for example, HIV-1). The compositions may be administered by any means of administration as long as a therapeutically effective amount for the treatment of pathogenic infection is delivered.

DETAILED DESCRIPTION OF THE INVENTION

Figure 1:
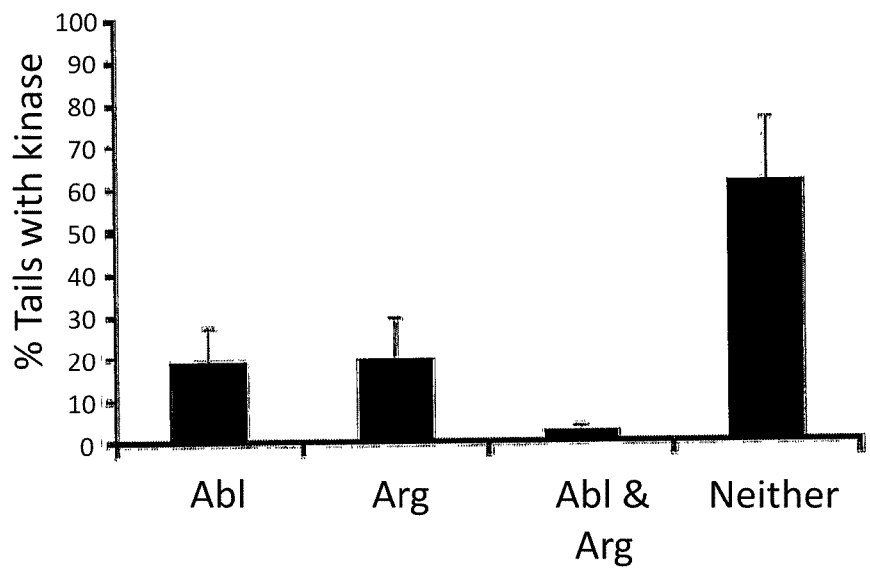
FIG. 1 shows that Abl- and Src-family tyrosine kinases localize in VV actin tails. (A) Quantitation of the percentage of tails in 3T3 cells containing Abl, Arg, both Abl and Arg, or neither Abl nor Arg. (B) Quantitation of distribution of Src-family kinases in VV actin tails.
Figure 1:
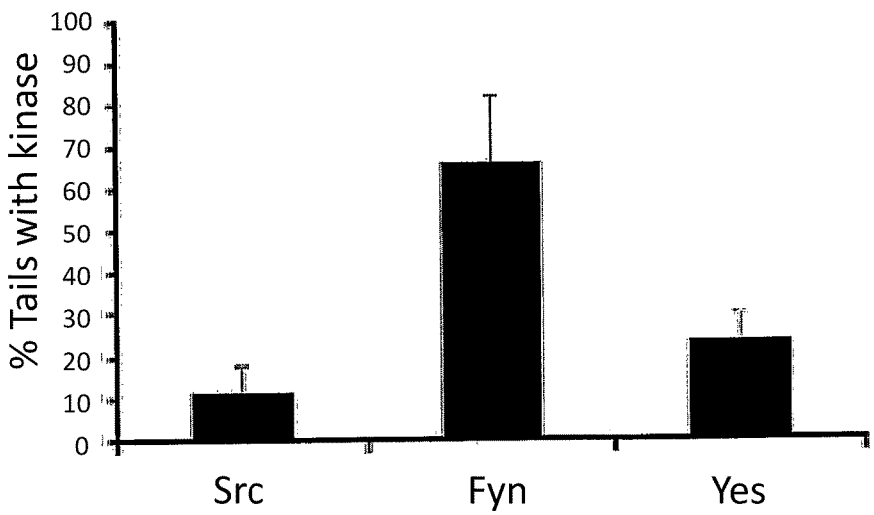

The present invention relates to the use of compounds that inhibit tyrosine kinases involved in pathogen-host cell interactions that are associated with or cause pathogenic infection. In particular, the present invention relates to the use of tyrosine kinase inhibitors to treat or prevent diseases associated with infection from microbial pathogens, including bacterial and viral pathogens such as *Escherichia coli, Helicobacter pylori, Listeria monocytogenes, Salmonella typhimurium, Shigella flexneri, Mycobacterium tuberculosis* (TB), Pox viruses including Vaccinia and variola viruses, polyoma viruses including JC and BK viruses, Herpes viruses, cytomegalovirus (CMV), and human immunodeficiency viruses (for example, HIV-1). Particularly, tyrosine kinase inhibitors for use in the present invention include Abl-family tyrosine kinase inhibitors such as imatinib mesylate, pyrido[2,3-d]pyrimidines, or pharmaceutically acceptable salts, enantiomers, analogs, esters, amides, prodrugs, metabolites, or derivatives thereof.

The tyrosine kinase inhibitors described therein can be used in the methods of the invention to treat or prevent any pathogenic infection that is associated with or caused by tyrosine kinase-mediated host-pathogen interactions, particularly microbial infection, and more particularly viral and bacterial infection. Without being bound by theory, it is believed that the tyrosine kinase inhibitors described herein target host cells and interfere with cellular mechanisms that allow for the interaction of these host cells with pathogens and in so doing prevent the pathogenic effects caused by the pathogen. Because cellular mechanisms regulating pathogen-host interactions are remarkably conserved, it is believed that the tyrosine kinase inhibitors described herein can be applied to combat infection by a wide range of pathogens. Such pathogens include various microbes such as bacteria, protozoa, viruses, algae, and fungi. In a preferred embodiment of the present invention, the pathogens are bacteria and viruses. Advantageously, the therapeutic approach described herein targets the host, rather than the pathogen as is seen with antibiotics, and therefore decreases the likelihood of the development of pathogen drug resistance.

In one embodiment, the present invention relates to the use of tyrosine kinase inhibitors to treat or prevent bacterial infections. Such infections include those caused by members of the following genera and species: *Agrobacterium tumefaciens, Aquaspirillum, Bacillus, Bacteroides, Bordetella pertussis, Borrelia burgdorferi, Brucella, Burkholderia, Campylobacter, Chlamydia, Clostridium, Corynebacterium diptheriae, Coxiella burnetii, Deinococcus radiodurans, Enterococcus, Escherichia, Francisella tularemsis, Geobacillus, Haemophilus influenzae, Helicobacter pylori, Lactobacillus, Listeria monocytogenes, Mycobacterium, Mycoplasma, Neisseria meningitidis, Pseudomonas, Rickettsia, Salmonella, Shigella, Staphylococcus, Streptococcus, Streptomyces coelicolor, Vibro*, and *Yersinia*. In a preferred embodiment, such infections include those caused by *Escherichia coli, Helicobacter pylori, Listeria monocytogenes, Salmonella typhimurium, Shigella flexneri*, and *Mycobacterium tuberculosis* (TB). In an other embodiment, such infections include those caused by pathogenic and/or diarrheagenic *Escherichia coli* strains, including enteropathogenic *Escherichia coli* (EPEC), enterohemmorhagic *Escherichia coli* (EHEC), uropathogenic *Escherichia coli* (UPEC), and enteroinvasive *Escherichia coli* (EIEC).

In another embodiment, the present invention relates to the use of tyrosine kinase inhibitors to treat viral infections. Such infections include those caused by members of the following virus families: Adenoviridae, Arenaviridae, Astroviridae, Bacteriophages, Baculoviridae, Bunyaviridae, Calciviridae; Coronaviridae, Deltavirus, Filoviridae, Flaviviridae, Geminiviridae, Hepadnaviridae, Herpesviridae, Nodaviridae, Orthomyxoviridae, Papovaviridae, Paramyxoviridae, Parvoviridae, Phycodnaviridae, Picornaviridae, Poxviridae, Reoviridae, Retroviridae, Rhabdoviridae, Tobamoviridae, and Toqaviridae. In a preferred embodiment, such infections include those caused by Pox viruses including Vaccinia and variola viruses, polyoma viruses including JC and BK viruses), Herpes viruses, cytomegalovirus (CMV), and human immunodeficiency viruses (for example, HIV-1).

In accordance with the methods of the present invention, the tyrosine kinase inhibitors described herein may be administered in combination with one another, for example, administering STI-X and STI-571, or with other compounds, particularly antipathogenic compounds. Such antipathogenic compounds include conventional antimicrobials. In other embodiments, one or more of the tyrosine kinase inhibitors described herein can be used in combination with other compounds such as cidofovir, for example, in cases related to smallpox, wherein the combination of these agents would provide for lower dosages of cidofovir to be administered, thereby decreasing the toxicity effects of this nucleoside analogue antiviral compound. Where the tyrosine kinase inhibitors of the present invention are administered as part of a combination therapy to treat or prevent pathogenic infection, they may be administered concurrently or sequentially, in either order, with the additional compound(s).

In one embodiment, tyrosine kinase inhibitors are administered to make vaccines more effective. For example, it is well known that immunization of neonates with live viruses does not contribute to acquired immunity because maternal antibodies neutralize the vaccine (Bot and Bona (2002) *Microbes Infect.* 4: 511). In one embodiment, administration of a tyrosine kinase inhibitor of the present invention allows for safe administration of higher doses of virus to overcome antibody response and permit acquisition of cellular immunity. In another embodiment, tyrosine kinase inhibitors of the present invention facilitate immune clearance of the pathogen. For some chronic viruses (e.g., HIV and polyoma), high viral loads have been found to compromise T cell function (Welsh (2001) *J. Exp. Med.* 193:F19). Thus, lowering the viral burden could permit recovery of T cell function and thereby facilitate clearance. In another embodiment, tyrosine kinase inhibitors of the present invention permit immunocompromised individuals to be vaccinated.

The tyrosine kinase inhibitors of the present invention are for administration in a living subject or patient, including a human being or an animal such as a laboratory monkey or mouse.

Tyrosine Kinase Inhibitor Compounds for Use in the Methods of the Invention

Currently, a number of families of tyrosine kinases are recognized, including Abl, Fes/Fer, Syk/Zap70, Jak, Tec, Fak, Ack, Src, and Csk. Of particular interest to the methods of the present invention are inhibitory compounds that target activity of several tyrosine kinase families, including, but not limited to, members of the Abl and Src families of tyrosine kinases. Thus, in one embodiment of the present invention, the tyrosine kinase inhibitor used to treat pathogenic infection inhibits at least members of the Abl family of tyrosine kinases, including c-Abl and c-Arg, though it is recognized that the inhibitors may also inhibit other family members.

Although ATP binding sites of tyrosine kinases are highly conserved, use of structural information obtained from X-ray crystallography and computer-assisted modeling based on kinase domain homology has led to the development of selective inhibitors. For Abl and BCR-Abl, STI-571 (also called imatinib mesylate or Gleevec®; Novartis Pharmaceuticals Corporation, East Hanover, N.J.; see also U.S. Pat. No. 5,521,184, herein incorporated by reference in its entirety) is one such inhibitor with reasonably high specificity that has proven clinically useful in treating Chronic Myelogenous Leukemia (CML; Druker et al. (2002) *Hematology* 2000 (Am. Soc. Hematol. Educ. Program):711-135; Goldman et al. (2001) *Blood* 98:2039). STI-571 has been used to treat stromal tumors, which are caused by dysregulation of c-Kit, a kinase with a structurally similar ATP binding site to Abl (Heinrich et al. (2000) *Blood* 96:925). Gleevec® is currently marketed as film-coated tablets containing imatinib mesylate equivalent to 100 mg or 400 mg of imatinib free base.

In one embodiment of the present invention, a method for preventing or treating a bacterial infection or a viral infection is provided, comprising administering a therapeutically effective amount of imatinib mesylate (STI-571) to a subject in need thereof.

STI-571 is designated chemically as 4-[(4-Methyl-1-piperazinyl)methyl]-N-[4-methyl-3-[[4-(3-pyridinyl)-2-pyrimidinyl]amino]-phenyl]benzamide methanesulfonate, with the following structural formula:

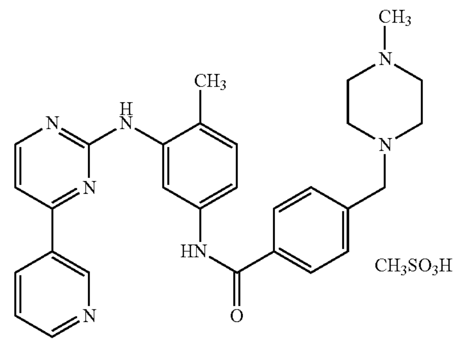

In another embodiment of the present invention, a method for preventing or treating a bacterial infection or a viral infection is provided, comprising administering a therapeutically effective amount of a benzylated derivative of imatinib mesylate, designated STI-X, to a subject in need thereof. STI-X has the following structural formula:

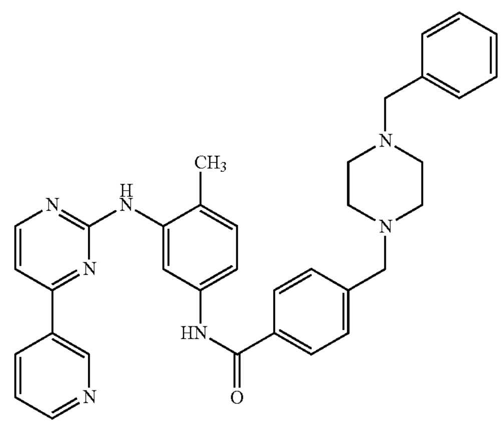 [SMILES: Cc1ccc(NC(=O)c2ccc(CN3CCN(Cc4ccccc4)CC3)cc2)cc1Nc1nccc(-c2cccnc2)n1]

According to another embodiment, the present invention encompasses compounds according to the formula:

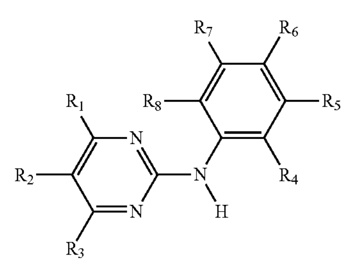

wherein:

$R_1$ is 4-pyrazinyl, 1-methyl-1H-pyrrolyl, amino-, or amino-lower alkyl-substituted phenyl wherein the amino group in each case is free, alkylated, or acylated, 1H-indolyl or 1H-imidazolyl bonded at a five-membered ring carbon atom, or unsubstituted or lower alkyl-substituted pyridyl bonded at a ring carbon atom and unsubstituted or substituted at the nitrogen atom by oxygen;

$R_2$ and $R_3$ are each independently of the other hydrogen or lower alkyl, one or two of the radicals $R_4$, $R_5$, $R_6$, $R_7$, and $R_8$ are each nitro, fluoro-substituted lower alkoxy or a radical of the formula —N($R_9$)—C(=X)—(Y)$_n$—$R_{10}$;

wherein:

$R_9$ is hydrogen or lower alkyl;

X is oxo, thio, imino, N-lower alkyl-imino, hydroximino, or O-lower alkyl-hydroximino;

Y is oxygen or the group NH, n is 0 or 1; and $R_{10}$ is an aliphatic radical having at least 5 carbon atoms, or an aromatic, aromatic-aliphatic, cycloaliphatic, cycloaliphatic-aliphatic, heterocyclic, or hetero-cyclicaliphatic radical;

and the remaining radicals $R_4$, $R_5$, $R_6$, $R_7$, and $R_8$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified, or esterified hydroxy, free, alkylated or acylated amino or free or esterified carboxy;

or a salt of such a compound having at least one salt-forming group. See, for example, U.S. Pat. No. 5,521,184, herein incorporated by reference in its entirety.

According to another embodiment, the invention encompasses compounds according to the formula

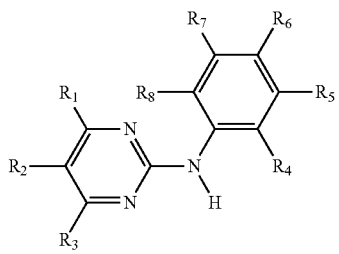

wherein $R_1$ is 4-pyrazinyl, 1-methyl-1H-pyrrolyl, amino-, or amino-lower alkyl-substituted phenyl wherein the amino group in each case is free, alkylated by one or two lower alkyl radicals or acylated by lower alkanoyl or by benzoyl, 1H-indolyl or 1H-imidazolyl bonded at a five-membered ring carbon atom, or unsubstituted or lower alkyl-substituted pyridyl bonded at a ring carbon atom and unsubstituted or substituted at the nitrogen atom by oxygen;

$R_2$ and $R_3$ are each independently of the other hydrogen or lower alkyl, one or two of the radicals $R_4$, $R_5$, $R_6$, $R_7$, and $R_8$ are each nitro, fluoro-substituted lower alkoxy or a radical of the formula —N($R_9$)—C(=X)—(Y)$_n$—$R_{10}$;

wherein:

$R_9$ is hydrogen or lower alkyl;

X is oxo, thio, imino, N-lower alkyl-imino, hydroximino, or O-lower alkyl-hydroximino;

Y is oxygen or the group NH, n is 0 or 1; and $R_{10}$ is an aliphatic hydrocarbon radical having 5-22 carbon atoms, a phenyl or naphthyl radical each of which is unsubstituted or substituted by cyano, lower alkyl, hydroxyl-lower alkyl, amino-lower alkyl, (4-methyl-piperazinyl)-lower alkyl, trifluoromethyl, hydroxy, lower alkoxy, lower alkanoyloxy, halogen, amino, lower alkylamino, di-lower alkylamino, lower alkanoylamino, benzolylamino, carboxy or by lower alkoxycarbonyl, or phenyl-lower alkyl wherein the phenyl radical is unsubstituted or substituted as indicated above, a cycloalkyl or cycloalkenyl radical having up to 30 carbon atoms, cycloalkyl-lower alkyl or cycloalkenyl-lower alkyl each having up to 30 carbon atoms in the cycloalkyl or cycloalkenyl moiety, a monocyclic radical having 5 or 6 ring members and 1-3 ring hetero atoms selected from nitrogen, oxygen, and sulfur, to which radical one or two benzene radicals may be fused, or lower alkyl substituted by such a monocyclic radical;

and the remaining radicals $R_4$, $R_5$, $R_6$, $R_7$, and $R_8$ are each independently of the others hydrogen, lower alkyl that is unsubstituted or substituted by amino, lower alkylamino, di-lower alkylamino, piperazinyl, piperidinyl, pyrrolidinyl, or by morpholinyl, or lower alkanoyl, trifluoromethyl, hydroxy, lower alkoxy, lower alkanoyloxy, halogen, amino, lower alkylamino, di-lower alkylamino, lower alkanoylamino, benzoylamino, carboxy, or lower alkoxycarbonyl, or a salt of such a compound having at least one salt-forming group. See, for example, U.S. Pat. No. 5,521,184, herein incorporated by reference in its entirety.

Cancer patients do develop resistance to STI-571, because inhibition of cell growth is a strong selection. This tendency to develop resistance to STI-571 has led to the search for more potent tyrosine kinase inhibitors, such as pyrido[2,3-d]pyrimidine (PD) compounds. PDs display more potency, though they differ in substrate specificity somewhat from STI-571 and, in addition to inhibiting Abl-family tyrosine kinases can also inhibit Src-family kinases, PDGFR, and FGFR kinases (Schindler et al. (2000) *Science* 289(5486):1938-1942; Wisniewski et al. (2002) *Cancer Res.* 62(15):4244-4255; Dorsey et al. (2000) *Cancer Res.* 60:3127; Kraker et al. (2000) *Biochem. Pharmacol.* 60:885). PDs only competitively inhibit ATP binding when the kinases are active.

In one embodiment of the present invention, a method for preventing or treating a bacterial infection or a viral infection is provided, comprising administering a therapeutically effective amount of a pyrido[2,3-d]pyrimidine to a subject in need thereof. Pyrido[2,3-d]pyrimidines that may be used according to the present invention include compounds as described in Kraker et al. (2000) *Biochem. Pharmacol.* 60(7): 885-898; and synthesized using methods adopted from Klutchko et al. (1998) *J. Med. Chem.* 41:3276-3292 and Boschelli et al. (1998) *J. Med. Chem.* 41:4365-4377. Such compounds include those represented by the following structural formula:

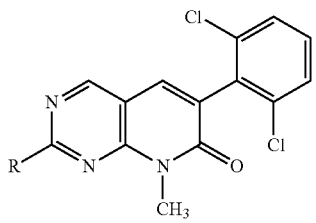

wherein R equals:

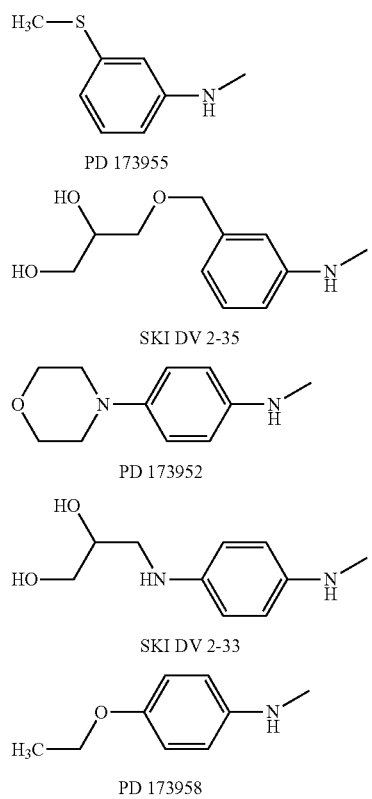

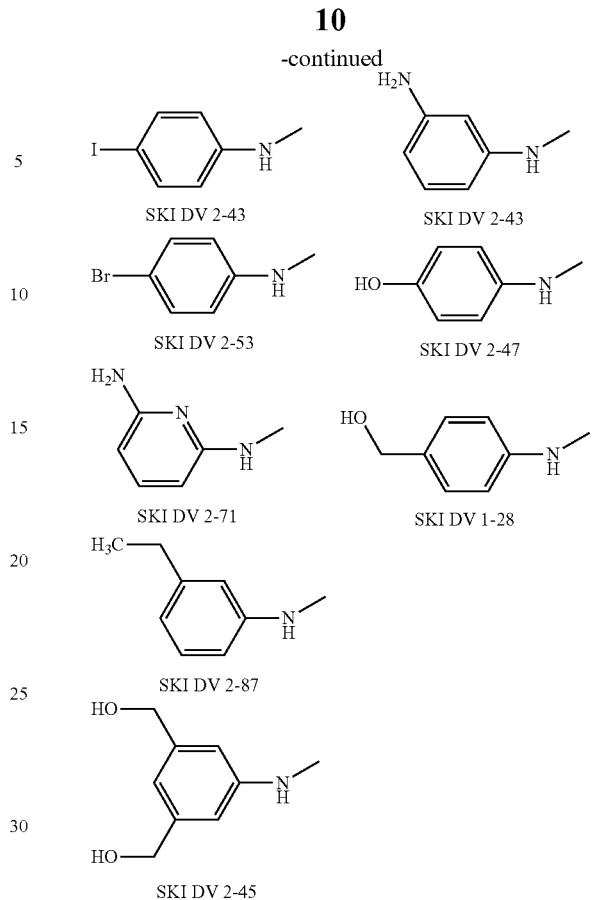

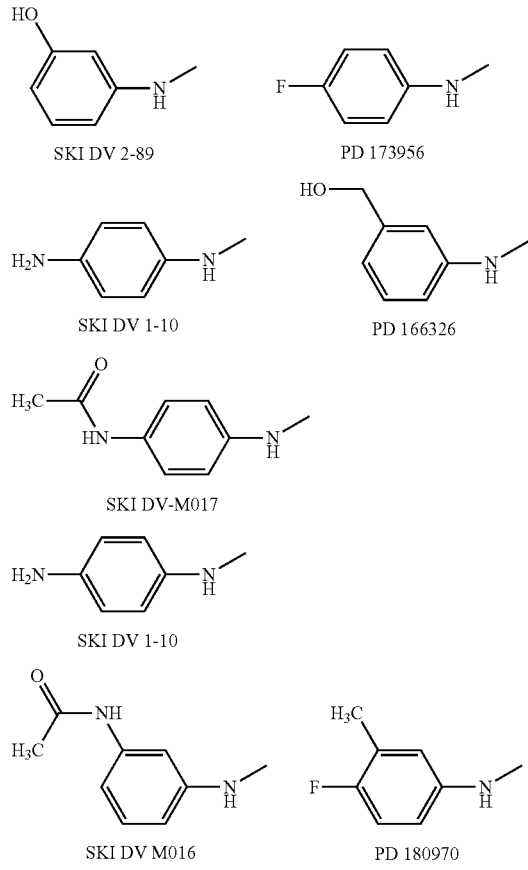

In another embodiment, the pyrido[2,3-d]pyrimidine selected for use according to the present invention is selected from the group consisting of:

a. PD 166326 (6-(2,6-Dichlorophenyl)-2-(3-hydroxymethylphenylamino)-8-methyl-8H-pyrido[2,3-d]pyrimidin-7-one);

b. PD 173952(6-(2,6-Dichlorophenyl)-8-methyl-2-(4-morpholinophenylamino)-8H-pyrido[2,3-d]pyrimidin-7-one);

c. PD173955 (6-(2,6-Dichlorophenyl)-8-methyl-2-(3-methylsulfanyl-phenyl amino)-8H-pyrido[2,3-d]pyrimidin-7-one);

d. PD173956 (6-(2,6-Dichlorophenyl)-2-(4-fluorophenylamino)-8-methyl-8H-pyrido[2,3-d]pyrimidin-7-one);

e. PM 73958 (6-(2,6-Dichlorophenyl)-2-(4-ethoxyphenylamino)-8-methyl-8H-pyrido[2,3-d]pyrimidin-7-one); and f. PD180970 (6-(2,6-Dichlorophenyl)-2-(4-fluoro-3-methylphenyl amino)-8-methyl-8H-pyrido[2,3-d]pyrimidin-7-one).

BMS-354825 is another tyrosine kinase inhibitor that has been shown useful in cases of STI-571 resistance. BMS-354825 is a synthetic small-molecule inhibitor of SRC-family kinases that binds Abl with less stringent conformational requirements and has been shown to inhibit Abl-tyrosine family kinases with two-log increased potency relative to STI-571 (Shah et al. (2004) *Science* 305:399-401).

Thus, in one embodiment of the present invention, a method for preventing or treating a bacterial infection or a viral infection is provided, comprising administering a therapeutically effective amount of BMS-354825, also called [N-(2-chloro-6-methylphenyl)-2-(6-(4-(2-hydroxyethyl)piperazin-1-yl)-2-methylpryimidin-4-ylamino)thiazole-5-carboxamide and having the following structure.

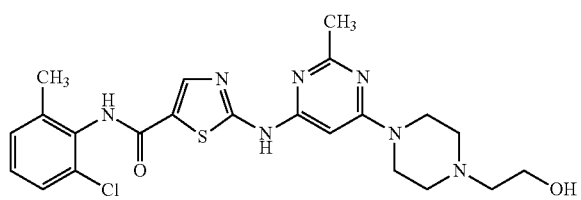 [SMILES: Cc1nc(Nc2ncc(C(=O)Nc3c(C)cccc3Cl)s2)cc(N2CCN(CCO)CC2)n1]

It is to be understood that the present invention encompasses the use not only of the specific compounds described above, but also any pharmaceutically acceptable salts, enantiomers, analogs, esters, amides, prodrugs, metabolites, or derivatives thereof.

Pharmaceutical Compositions

Because tyrosine kinase inhibitors are already the subject of drug development or are in use to treat certain cancers, data has established that they are well tolerated in humans even for extended periods (months), and are not toxic. The drugs can be ingested orally, are stable at room temperature, and are simple and inexpensive to manufacture.

In one embodiment of the present invention, a method of treating or preventing pathogenic infection, particularly microbial infection, comprises administering to a living subject in need of such treatment an effective amount of a pharmaceutical composition suitable for administration to the living subject where the pharmaceutical composition comprises: (a) at least one tyrosine kinase inhibitor in an amount effective for augmenting an inhibitable response from a host cell of the living subject responsive to at least one pathogen, particularly a microbe; and (b) a pharmaceutically acceptable carrier suitable for administration to the living subject.

In another embodiment, the present invention also relates to pharmaceutical compositions suitable for administration to a living subject, comprising: (a) at least one tyrosine kinase inhibitor in an amount effective for augmenting an inhibitable response from a host cell of the living subject responsive to at least one bacteria; and (b) a pharmaceutically acceptable carrier suitable for administration to a living subject.

In another embodiment, the present invention also relates to pharmaceutical compositions suitable for administration to a living subject, comprising: (a) at least one tyrosine kinase inhibitor in an amount effective for augmenting an inhibitable response from a host cell of the living subject responsive to at least one virus; and (b) a pharmaceutically acceptable carrier suitable for administration to a living subject.

The pharmaceutically acceptable carrier can be suitable for oral administration to the living subject, and the pharmaceutical composition is administered to the living subject orally. The pharmaceutically acceptable carrier can also be suitable for nasal administration to the living subject, and the pharmaceutical composition is administrated to the living subject nasally. Or the pharmaceutically acceptable carrier is suitable for rectal administration to the living subject, and the pharmaceutical composition is administrated to the living subject rectally. Moreover, the pharmaceutically acceptable carrier can be suitable for intravenous administration to the living subject, and the pharmaceutical composition is administrated to the living subject intravenously. Furthermore, the pharmaceutically acceptable carrier can be suitable for inoculative administration to the living subject, and the pharmaceutical composition is administrated to the living subject inoculatively. Additionally, the pharmaceutically acceptable carrier can be suitable for hypodermic administration to the living subject, and the pharmaceutical composition is administrated to the living subject hypodermically. Thus, depending upon the pathogenic infection to be treated or prevented, the pharmaceutical composition comprising a tyrosine kinase inhibitor described herein can be administered by any suitable route, including, but not limited to, orally, nasally, buccally, sublingually, intravenously, transmucosally, rectally, topically, transdermally, subcutaneously, by inhalation, or intrathecally.

In particular, in another embodiment, these pharmaceutical compositions may be in the form of orally administrable suspensions, drinking solutions, or tablets; nasal sprays or nasal drops; or olegenous suspensions or suppositories.

When administered orally as a suspension, compositions of the present invention are prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art. Components in the formulation of a mouthwash or rinse include antimicrobials, surfactants, cosurfactants, oils, water and other additives such as sweeteners/flavoring agents known in the art.

When administered by a drinking solution, the composition comprises one or more of the tyrosine kinase inhibitor compounds described herein dissolved in drinking liquid such as water, with appropriate pH adjustment, and with carrier. The compound dissolved in the drinking liquid is an amount sufficient to give a concentration in the bloodstream on the order of 1 nM and above, preferably in an effective amount that is effective in vivo.

When administered nasally, these compositions are prepared according to techniques well known in the art of pharmaceutical formulation and may be prepared as solutions in saline, employing benzyl alcohol or other suitable preservatives, absorption promoters to enhance bioavailability, and/or other solubilizing or dispersing agents known in the art (see, for example, Ansel et al. (1999) *Pharmaceutical Dosage Forms and Drug Delivery Systems* ($7^{th}$ ed.).

Preferably these compositions and formulations are prepared with suitable nontoxic pharmaceutically acceptable ingredients. These ingredients are known to those skilled in the preparation of nasal dosage forms and some of these can be found in *Remington's Pharmaceutical Sciences* (18th ed., Mack Publishing Company, Eaton, Pa.; 1990), a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, jelling agents, or buffering and other stabilizing and solubilizing agents may also be present.

The formulations of this invention may be varied to include: (1) other acids and
bases to adjust the pH; (2) other tonicity-imparting agents such as sorbitol, glycerin, and dextrose; (3) other antimicrobial preservatives such as other parahydroxy benzoic acid esters, sorbate, benzoate, propionate, chlorbutanol, phenylethyl alcohol, benzalkonium chloride, and mercurials; (4) other viscosity imparting agents such as sodium carboxymethylcellulose, microcrystalline cellulose, polyvinylpyrrolidone, polyvinyl alcohol and other gums; (5) suitable absorption enhancers; (6) stabilizing agents such as antioxidants, like bisulfate and ascorbate, metal chelating agents such as sodium edentate, and drug solubility enhancers such as polyethylene glycols.

The above nasal formulations can be administered as drops, sprays, or by any other intranasal dosage form. Optionally, the delivery system can be a unit dose delivery system. The volume of solution or suspension delivered per dose can be anywhere from 5 to 500 microliters, and preferably 5 to 200 microliters. Delivery systems for these various dosage forms can be dropper bottles, plastic squeeze units, atomizers, and the like in either unit dose or multiple dose packages. Lozenges can be prepared according to U.S. Pat. No. 3,439,089, herein incorporated by reference for these purposes.

When rectally administered in the form of suppositories, these compositions may be prepared by mixing the drug with a suitable non-irritating excipient, such as cocoa butter, synthetic glyceride esters, or polyethylene glycols, which are solid at ordinary temperatures, but liquefy and/or dissolve in the rectal cavity to release the drug.

Dosage levels on the order of 1 mg/day or above may be useful in the treatment or prevention of pathogenic infections and related diseases within a host organism as noted herein above. In one embodiment of the present invention, a patient in need of treatment or prevention of pathogenic infection is administered a tyrosine kinase inhibitor described herein in an amount equal to or greater than about 1 mg/day, equal to or greater than about 5 mg/day, equal to or greater than about 10 mg/day, equal to or greater than about 20 mg/day, equal to or greater than about 30 mg/day, equal to or greater than about 40 mg/day, equal to or greater than about 50 mg/day, equal to or greater than about 60 mg/day, equal to or greater than about 70 mg/day, equal to or greater than about 80 mg/day, equal to or greater than about 90 mg/day, equal to or greater than about 100 mg/day, equal to or greater than about 110 mg/day, equal to or greater than about 120 mg/day, equal to or greater than about 130 mg/day, equal to or greater than about 140 mg/day, equal to or greater than about 150 mg/day, equal to or greater than about 160 mg/day, equal to or greater than about 170 mg/day, equal to or greater than about 180 mg/day, equal to or greater than about 190 mg/day, equal to or greater than about 200 mg/day, equal to or greater than about 210 mg/day, equal to or greater than about 220 mg/day, equal to or greater than about 230 mg/day, equal to or greater than about 240 mg/day, equal to or greater than about 250 mg/day, equal to or greater than about 260 mg/day, equal to or greater than about 270 mg/day, equal to or greater than about 280 mg/day, equal to or greater than about 290 mg/day, equal to or greater than about 300 mg/day, equal to or greater than about 310 mg/day, equal to or greater than about 320 mg/day, equal to or greater than about 330 mg/day, equal to or greater than about 340 mg/day, equal to or greater than about 350 mg/day, equal to or greater than about 360 mg/day, equal to or greater than about 370 mg/day, equal to or greater than about 380 mg/day, equal to or greater than about 390 mg/day, equal to or greater than about 400 mg/day, equal to or greater than about 410 mg/day, equal to or greater than about 420 mg/day, equal to or greater than about 430 mg/day, equal to or greater than about 440 mg/day, equal to or greater than about 450 mg/day, equal to or greater than about 460 mg/day, equal to or greater than about 470 mg/day, equal to or greater than about 480 mg/day, equal to or greater than about 490 mg/day, equal to or greater than about 500 mg/day, equal to or greater than about 510 mg/day, equal to or greater than about 520 mg/day, equal to or greater than about 530 mg/day, equal to or greater than about 540 mg/day, equal to or greater than about 550 mg/day, equal to or greater than about 560 mg/day, equal to or greater than about 570 mg/day, equal to or greater than about 580 mg/day, equal to or greater than about 590 mg/day, or equal to or greater than about 600 mg/day, for a patient having approximately 70 kg body weight. In some embodiments, the dose to be administered ranges from about 1 mg/day to about 1000 mg/day, including about 10 mg/day, 20 mg/day, 30 mg/day, 40 mg/day, 50 mg/day, 60 mg/day, 70 mg/day, 80 mg/day, 90 mg/day 100 mg/day, 125 mg/day, 150 mg/day, 175 mg/day, 200 mg/day, 225 mg/day, 250 mg/day, 275 mg/day, 300 mg/day, 350 mg/day, 400 mg/day, 450 mg/day, 500 mg/day, 550 mg/day, 600 mg/day, 650 mg/day, 700 mg/day, 750 mg/day, 800 mg/day, 850 mg/day, 900 mg/day, 950 mg/day, 1000 mg/day, and other such values between about 1 mg/day to about 1000 mg/day, for a patient having approximately 70 kg body weight. It will be understood, however, that the specific dose level and frequency of dosage for any particular patient may be varied and will depend upon a variety of factors including the activity of the specific salt or other form employed, the metabolic stability and length of action of that compound, the age, body weight, general health, sex, diet, mode and time of administration, rate of excretion, drug combination, the severity of the particular condition, and the host undergoing therapy.

In one preferred regimen, such dosages can be administered to a subject in need thereof by either nasal spray or by oral lozenge.

The effectiveness of using the pharmaceutical compositions of the present invention to treat or prevent a specific pathogenic infection, particularly microbial infection, may vary, for example, depending on the infectious agent, stage of infection, severity of infection, age, weight, and sex of the patient, and the like.

"Treatment" is herein defined as the application or administration of a tyrosine kinase inhibitor described herein to a subject, where the subject has a pathogenic infection as noted elsewhere herein, a symptom associated with a pathogenic infection, or a predisposition toward development of a pathogenic infection, where the purpose is to cure, heal, alleviate, relieve, alter, remedy, ameliorate, improve, or affect the pathogenic infection, any associated symptoms of the pathogenic infection, or the predisposition toward the development of the pathogenic infection. By "treatment" is also intended the application or administration of a pharmaceutical composition comprising a tyrosine kinase inhibitor described herein to a subject, where the subject has a pathogenic infection as noted elsewhere herein, a symptom associated with a pathogenic infection, or a predisposition toward development of a pathogenic infection, where the purpose is to cure, heal, alleviate, relieve, alter, remedy, ameliorate, improve, or affect the pathogenic infection, any associated symptoms of the pathogenic infection, or the predisposition toward the development of the pathogenic infection.

The tyrosine kinase inhibitors described herein are useful in treating or preventing pathogenic infections as noted herein above. Treatment or prevention of pathogenic infection in the manner set forth herein is particularly useful for transplant patients, for example, kidney transplant patients, where emergence of pathogens, particularly polyoma viruses, for example, JC and BK, and pathogenic infection can diminish function of the transplanted organ. In like manner, HIV infection can destroy oligodendrocytes in the brain, leading to AIDS-related dementia. Thus, in addition to treating or preventing pathogenic infections as noted elsewhere herein, the tyrosine kinase inhibitors described herein can be used to control secondary infection in HIV-positive and AIDS patients and in patients receiving transplants, for example, kidney transplants, and to control AIDS-related dementia. Further, the tyrosine kinase inhibitors can be used prophylactically to prevent spread of infectious virions, for example, associated with Vaccinia infections, in immunocompromised individuals, including HIV-positive and AIDS patients and in patients receiving transplants.

EXPERIMENTAL

The following experiments examined the effects of tyrosine kinase inhibitors on the infection of host cells by pathogens, particularly bacterial and viral pathogens. Before describing these experiments in more detail, it will be helpful to provide a basic description of the pathogens studied and host-pathogen interactions.

Pathogenic *E. coli*, including enteropathogenic *E. coli* (EPEC) and enterohemmorhagic *E. coli* (EHEC), contaminate water and food supplies and cause infantile diarrhea. EPEC and EHEC are classified by NIAID as category B pathogens. In developing nations, EPEC causes sickness in some 20 million per year, killing 500,000 (Goosney et al. (2000) *Annu. Rev. Cell Dev. Biol.*, 16: 173). EHEC, causative agent of "raw hamburger disease," contaminates food and is associated with diarrhea and an often fatal consequence, hemolytic-uremic syndrome. EHEC possess two Shiga toxins, which cause the symptoms associated with hemolytic-uremic syndrome (Perna et al. (2001) *Nature*, 409(6819): 529-33).

EPEC, EHEC, and *Citrobacter (C.) rodentium* (mouse EPEC) form actin-filled membrane protrusions or "pedestals" beneath themselves on the surface of epithelial cells (Knutton et al. (1989) *Lancet* 2: 218; McDaniel et al. (1997) *Mol. Microbiol.*, 23: 399). Pedestals prevent phagocytosis, allow colonization of the host, and are required for subsequent development of disease (Goosney et al. (1999) *Infect. Immun.*, 67: 490; Jerse et al. (1990) *Proc. Natl. Acad. Sci. USA*, 87: 7839). The mechanisms by which pedestals form have been extensively investigated (Kalman et al. (1999) *Nat. Cell Biol.*, 1: 389). The development of both pedestals and diarrhea are critically dependent on the activation of a host tyrosine kinase beneath the bacterium, which phosphorylates a bacterial protein secreted into the host cell called Tir (Kenny et al. (1997) *Cell*, 91: 511; Kenny (1999) *Mol. Microbiol.*, 31: 1229). Upon binding of the bacterial ligand intimin, a host signal transduction cascade is initiated that leads to pedestal formation.

The watershed event in EPEC pathogenesis is the phosphorylation of EPEC Tir (Kenny (1999) *Mol. Microbiol.*, 31: 1229). Once phosphorylated, EPEC Tir facilitates recruitment and activation of host cell proteins, including Nck, N-WASP, and Arp2/3 complex, that initiate actin polymerization to construct and brace the pedestal Kalman et al. (1999) *Nat. Cell Biol.*, 1: 389; Lommel et al. (2001) *EMBO Rep.*, 2: 850; Gruenheid et al. (2001) *Nat. Cell Biol.*, 3: 85619; Rohatgi et al. (1999) *Cell*, 97: 221).

Vaccinia virus (VV) and variola viruses are members of the Poxviridae family that are 95% identical in sequence (Esposito et al. (1990) *Poxviruses*, in *Fields Virology*, D. M. Knipe, Editor, Raven Press: New York. p. 2336; Moss (1990) *Poxviridae: The Viruses and Their Replication*, in *Fields Virology*, D. M. Knipe, Editor. Raven Press: New York. p. 2336). VV western reserve (WR) strain serves as a vaccinating agent for variola major, the cause of smallpox. VV and variola enter mammalian cells, establish extranuclear replication "factories," and produce enveloped virions (Moss (1990) *Poxviridae: The Viruses and Their Replication*, in *Fields Virology*, D. M. Knipe, Editor. Raven Press: New York. p. 2336). These virions travel to the cell surface using microtubule motors and transit into apposing cells by polymerizing actin (Ploubidou et al. (2000) EMBO J., 19(15): p. 3932-44; Rietdorf et al. (2001) *Nat. Cell Biol.*, 3(11): p. 992-1000; Ward and Moss (2001) *J. Virol.*, 75(23): p. 11651-63; Ward and Moss (2001) *J. Virol.*, 75(10): p. 4802-13; Cudmore et al. (1996) *J. Cell Sci.*, 109 (Pt 7): p. 1739-47; Cudmore et al. (1997) *Trends Microbiol.*, 5(4): p. 142-8). There the virions polymerize actin to propel themselves through the host cell cytoplasm and towards the plasma membrane, where they exit the cell and enter apposing cells. Formation of actin "comets" is considered critical for vaccinia to spread from cell to cell. For actin-based motility, vaccinia relies on the recruitment of host cell molecules to the surface of the particle, including tyrosine kinases. Ultimately, the host cell undergoes cytolysis thereby releasing additional infectious particles.

Tyrosine and serine/threonine kinases are important for several aspects of viral infection. Actin-based motility depends on the activity of the host cell tyrosine kinases related to c-Src and Abl, and replication at least in part depends on a viral kinase, though the precise mechanism is less well understood (Frischknecht et al. (1999) *Nature* 401 (6756):926-929; Rempel et al. (1992) *J. Virol.* 66(7):4413-4426; Traktman et al. (1995) *J. Virol.* 69(10):6581-6587; Traktman et al. (1989) *J. Biol. Chem.* 264(36):21458-21461)

Upon entry of the pox virus into host cells, the virion moves to a juxtanuclear location where it replicates up to $10^4$ concatameric genomes (Moss (1990) *Poxviridae: The Viruses and Their Replication*, in *Fields Virology*, D. M. Knipe, Editor. Raven Press: New York, p. 2336). The concatamers ultimately form individual enveloped particles (called intracellular mature virions (IMVs), some of which are packaged in additional membranes to form intracellular enveloped virions (IEVs; Smith et al. (2003) *Annu. Rev. Microbiol.*, pp. 323-342). Cytolysis releases IMVs from the cell. Prior to cytolysis, however, IEVs travel towards the host cell periphery via a kinesin/microtubule transport system (Carter et al. (2003) *J. Gen. Virol.*, pp. 2443-2458; Hollinshead et al. (2001) *J. Cell Biol.*, pp. 389-402; Rietdorf et al. (2001) *Nat. Cell Biol.*, pp. 992-1000; Ward and Moss (2001) *J. Virol.*, pp., 11651-11663).

To exit the cell, the IEV particle fuses with the plasma membrane of the host cell to form a cell-associated enveloped virus (CEV), leaving behind one of its two outer membranes (Smith et al. (2003) *Ann. Rev. Microbiol., pp.*, 323-342; Smith et al. (2002) *J. Gen. Virol.*, pp. 2915-2931). CEVs either detach directly, or initiate actin polymerization to propel the particle on an actin-filled membrane protuberance towards an apposing cell and then detach (Smith et al. (2003) *Ann. Rev. Microbiol.*, pp., 323-342). Actin motility depends on Abl and Src family kinases whereas detachment of CEvs to form extracellular enveloped virus (EEV) depends on Abl family kinases (Smith et al. (2003) *Ann. Rev. Microbiol.*, pp., 323-342).

It is known that the protein encoded by the VV A36R gene (called A36R), located in the membrane surrounding the CEV, is required for actin polymerization and virulence (Wolffe et al. (1998) *Virology* pp. 20-26; Parkinson and Smith (1994) *Virology* pp. 376-390). The watershed event in actin polymerization and cell-to-cell spread is the phosphorylation of A36R tyrosine residues by a host cell tyrosine kinase (Newsome et al. (2004) *Science* 306:124-128; Frischknecht et al. (1999) *Nature* 401(6756):926-929). There is a remarkable homology between the EPEC Tir protein described above and the VV protein A36R, therefore using similar but not identical host signalling factors as EPEC to polymerize actin and exit from the host cell (Frischknecht and Way (2001) *Trends Cell Biol.* 11(1):30-38).

Previous reports suggest that the mammalian tyrosine kinase c-Src localizes to virions (Frischknecht et al. (1999) *Nature* 401(6756):926-929). Moreover, the release of virions from microtubules and nucleation of actin to form actin tails depends on phosphorylation of A36R by Src or other kinases (Newsome et al. (2004) *Science* 306:124-128; Frischknecht et al. (1999) *Nature* 401(6756):926-929; Kalman et al. (1999) *Nat. Cell. Bio.* 1:389-391). Once phosphorylated, A36R facilitates detachment of kinesin and recruitment and activation of host cell proteins, including Nck, Grb2, N-WASP, and the Arp2/3 complex, which initiate actin polymerization beneath the particle (Frischknecht and Way (2001) *Trends Cell Biol.* 11(1):30-38; Moreau et al. (2000) *Nat. Cell Biol.*, pp. 441-448; Scaplehom et al. (2002) *Curr. Biol.*, pp. 740-745). Indeed vaccinia uses mechanisms similar to those used by *Shigella flexneri* to propel itself through the host cytoplasm. For example, both *Shigella* and Vaccinia recruit and activate N-WASP and the Arp2/3 complex as a means of polymerizing actin (Frischknecht and Way (2001) *Trends Cell Biol.* 11(1):30-38).

Experiment 1

Src and Abl Family Tyrosine Kinases Participate in VV Actin Motility and Release of Infectious Virions The purpose of the present experiment was to test whether several tyrosine kinases, including members of the Src family (c-Src, c-Fyn and c-Yes) and Abl family (c-Abl and c-Arg), are required for actin motility and release of infectious EEVs. Fibroblasts lacking one or more of these kinases in conjunction with potent inhibitors of these enzymes were used (Garcia-Echeverria et al. (2000) *Med. Res. Rev.*, pp. 28-57).

Methods

3T3 cells, 3T3 cells derived from $Abl^{-/-}/Arg^{-/-}$ mice, or 3T3 cells derived from $Src^{-/-}/Fyn^{-/-}/Yes^{-/-}$ mice were grown on glass coverslips in DMEM containing serum and incubated for sixteen hours at 37° C. with VV (strain WR) or VVGFP-B5R at a proper amount of m.o.i. For some experiments, cells were transfected one to two days prior to infection with plasmid vectors using Fugene-6 (Roche). Abl-T315I, Argl-T314I, and Src-T338M were constructed using Quik-Change site directed mutagenesis technology. PD compounds PD166326, SKI-DRV-1-10, were synthesized as described elsewhere herein, and were indistinguishable in their effects in all assays. STI-571 was synthesized as described elsewhere herein. STI-571, PD compounds, and PP2 (Calbiochem) were dissolved in 100% DMSO. PD, PP2, or DMSO was added to cells either one hour prior to infection. For "reversal" experiments, compound or DMSO was added to cells fourteen hours after addition of VV, and the cells fixed fifteen minutes to two hours subsequently.

For immunofluorescence analysis, cells were fixed in 2% formaldehyde and permeablized in Triton-X-100. VV was recognized by staining with 4,6-diamidino-2-phenylindole (DAPI; 1 µg/ml; Sigma), and actin tails by staining with FITC-phalloidin (1 µg/ml; Molecular Probes). The primary antibodies and concentrations used in this study were as follows: α-WASP pAb (affinity purified, 1:200 dilution), α-HA mAb (3F10; 0.01 µg/ml, Roche), α-Nck mAb (1 µg/ml; Oncogene Research), α-Abl mAb (AB3; 0.5 µg/ml for overexpressed Abl proteins; 50 µ·g/ml for endogenous Abl proteins; 8E9; 0.05 µg/ml; Pharmingen), u-Src pAb (0.1 µg/ml; Santa Cruz), α-Arg, α-pY412, and α-TW2.3 mAb (ascites, 1:2000 for microscopy). Cells expressing exogenous c-Abl-WT were distinguished by relatively high fluorescence intensity with lower α-AbI mAb concentrations. Thus images were acquired with much shorter exposures than those used to detect endogenous c-Abl-like protein. Secondary antibodies were obtained from Jackson Immunochemicals.

For immunoprecipitation experiments, uninfected cells or cells infected with VV were washed three times with cold phosphate buffered saline and lysed for 30 minutes at 4° C. in 20 mM Tris, pH 7.2, 150 mM NaCl, 5 mM EDTA, 1% Triton-X 100, 10% glycerol, 1 mM sodium orthovanadate and protease inhibitors (Complete protease inhibitor mix; Roche). Samples were centrifuged for 20 mM. at 10,000×g. Samples were incubated with primary antibody (α-YFP, α-Src, or α-Abl) for two hours at 4° C., and for an additional hour with protein G beads. The beads were washed with lysis buffer and analyzed by immunoblotting or used in in vitro kinase assays. For in vitro kinase assays, GST-Crk (for Abl and Arg) was used as a substrate and incubated for 30 minutes at 23° C. with 10 µM ATP in 20 µl Kinase Assay Buffer (25 mM Tris, 10 mM $MgCl_2$, 1 mM DTT) together with c-Abl, c-Abl-T315I, YFP-Arg, or YFP-Arg-T3141, previously transfected into cells and isolated on agarose beads by immunoprecipitation with α-Abl or α-YFP antibodies. Samples were then subjected to SDS-PAGE transferred to PVDF membrane and immunoblotted with α-phosphotyrosine antibody 4G10, or α-Abl mAb AB3, or α-YFP.

Images were acquired with a scientific-grade cooled charge-coupled device (Cool-Snap HQ) on a multi-wavelength wide-field three-dimensional microscopy system (Intelligent Imaging Innovations) based on a Zeiss 200M inverted microscope using a 63×N.A.1.4 lens (Zeiss). Immunofluorescent samples were imaged at room temperature using a standard Sedat filter set (Chroma) in successive 0.20 µm focal planes through the samples, and out-of-focus light was removed with a constrained iterative deconvolution algorithm.

For plaque assays, cells were seeded in 24-well dishes, grown to confluence, and incubated with VV-WR at various serial dilutions. After one hour the cells were washed to remove excess virus, and the cells were incubated for an additional 3-4 days. Cells were then fixed and stained with 20% ethanol and 4% coomasie blue to visualize plaques. For measurements of secreted EEVs, media was removed 24 hours after infection, added to uninfected 3T3 cell monolayers, and the number of plaques assessed 4 days subsequently. To determine whether different cell lines were infected (plaque reduction assays), cell monolayers were sonicated to release viral particles in the cell, and then centrifuged to remove cellular debris. The supernatant was then serially diluted and added to monolayes of uninfected 3T3 cells, and the number of plaques assessed after 3-4 days.

Six week old C57/B16 mice (Jackson laboratories) were infected by intranasal inoculation with $10^4$ pfu/ml VV, a titre at which all mice died within 7 days. For mouse experiments, PD-166326 was dissolved in 30% DMSO, 30% PEG-400, and 37% saline, and STI-571 (methcylate salt) was dissolved in saline. PD-166326 (30 mg/kg/day) was administered by intraperitoneal injection twice daily beginning 2-6 hrs prior to infection and STI-571 (100 mg/kg/day) was administered from subcutaneously implanted osmotic pumps. Quantitation of drug levels in the blood of control animals by HPLC/MS as described previously indicated that PD 166326 was present. The level of STI-571 in the blood was not determined. At these drug concentrations, no loss in weight or other adverse effects in uninfected animals were observed. Thus the drug appeared nontoxic.

Results

Src, Fyn, Yes, Abl and Arg Localize in VV Actin Tails.

To test the hypothesis that Src and Abl-family tyrosine kinases participate in VV actin motility, it was first determined whether endogenous proteins resembling Src or Abl localized on the virion at the tip of the actin tail. 3T3 cells were exposed to VV for 15 hrs, and then stained with antibodies against Src, Fyn, Yes, Abl, and Arg. Infected cells were recognized by staining with DAPI which recognized extranuclear replication centers ("RC"), or by staining with a-TW2.3, an antibody that recognizes a vaccinia protein expressed early in infection.

The virion itself was recognized by DAPI staining or by fluorescence of a GFP-B5R fusion protein localized in the inner membrane of the virion. Actin tails may be seen as intense phalloidin staining directly apposed to the virion. An endogenous protein recognized by the antibodies against the Abl related kinase Arg was enriched at the tips of the actin tails relative to the cytoplasm. Likewise, endogenous proteins recognized by the α-Abl mAb 8E9, α-Src pAb, α-Fyn mAb, and α-Yes mAb were also enriched at the tips of the actin tails relative to the cytoplasm. Identical results were obtained with other antibodies (e.g. AB3 for Abl).

The antibodies were specific and did not recognize epitopes in cells lacking these kinases, and showed no cross-reactivity with other family members as judged by transfection experiments in cells lacking Src-family or Abl-family kinases. Notably, each kinase was detectable in only a fraction of the actin tails. For example, c-Abl was detectable in some tails but not in others within the same cell. Moreover, staining with combinations of antibodies (e.g., α-Abl mAb together with α-Arg pAb), indicated that tails containing one kinase did not generally contain detectable levels of another kinase type, though both Abl and Arg kinases were evident in approximately 5% of tails.

Similar results were obtained with combinations of other anti-kinase antibodies, though because many were of similar isotype, testing of all combinations was not feasible. FIG. 1A shows the percentage of tails in 3T3 cells containing Abl, Arg, both Abl and Arg, or neither Abl nor Arg. Note most tails contain one or the other kinase but few contain both. In addition, FIG. 1B shows the distribution of Src-family kinases in VV actin tails. Of the five Src- and Abl-family kinases, proteins resembling c-Fyn were the most frequently observed in actin tails. Finally, no evidence was found for localization of other tyrosine kinases including PDGFR, FGFR, Lck, FAK, Ntk, Lyn, Jak1, Csk, Tyk2, and Pyk2, suggesting that localization is specific for Src- and Abl-family kinases.

To insure that the anti-kinase antibodies were indeed specific, it was next determined whether localization and distribution of exogenously expressed kinases was the same as that observed with endogenous proteins. To do this it was assessed whether yellow fluorescent protein-tagged c-Arg (YFP-c-Arg), untagged or haemagglutinin A (HA)-tagged c-Abl (HA-c-Abl) localized in actin tails. YFP-c-Arg was present in only a fraction of actin tails in transfected cells, in general agreement with results obtained with staining for the endogenous protein. Even in cells expressing high levels of YFP-c-Arg, some tails contained no YFP-c-Arg, suggesting that the localization of overexpressed kinase is specific. Additionally, co-localization was not observed for other overexpressed proteins including: Green or Yellow Fluorescent Protein, or the kinase Hck, detected with α-Hck pAb (not shown). Together these results suggest that overexpressed tyrosine kinases can specifically localize in actin tails, and that, like endogenous proteins, transfected kinases do not localize to all tails.

c-Abl or c-Arg are activated in VV actin tails.

To determine whether c-Abl or c-Arg were active in VV actin tails, an antibody stain was used that recognizes the phosphorylated Y412 (α-PY412) in the activation loop domain of both proteins (Pluk et al., (2002) Cell, 247-259). However, because the activation loop epitope recognized by the α-PY412 pAb is identical in c-Abl and c-Arg, the antibody cannot discriminate between the two proteins in a fluorescence experiment. Staining with α-PY412 was evident in the tails. Moreover, staining with α-PY412 pAb was specific for c-Abl or c-Arg, and was not evident in tails formed in cells lacking c-Abl and c-Arg.

Actin Tails Form on Cell Lines Deficient in Src- or Abl-Family Tyrosine Kinases.

To determine whether Src and/or Abl-family tyrosine kinases were necessary for actin tail formation, 3T3 cells were infected that were derived from mice lacking c-Src (Src$^{-/-}$), c-Src and Yes (Src$^{-/-}$/Yes$^{-/-}$), c-Fyn and c-Yes (Fyn$^{-/-}$/Yes$^{-/-}$) or c-Src, c-Fyn, and c-Yes (Src$^{-/-}$/Fyn$^{-/-}$/Yes$^{-/-}$), or from mice lacking c-Abl alone (Abl$^{-/-}$), c-Arg alone (Arg$^{-/-}$), or both c-Abl and c-Arg (Abl$^{-/-}$/Arg$^{-/-}$). These cells were exposed to VV or GFP-VV and stained with Cy3 phalloidin.

Figure 2:
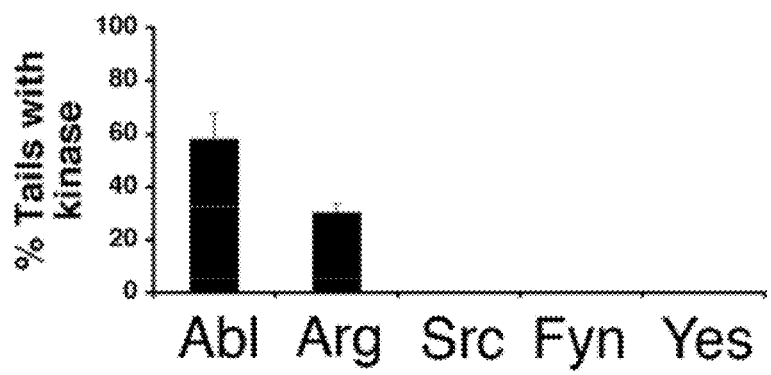
FIG. 2 shows a quantitation of the distribution of ABL and Src-family kinases in VV actin tails for: (A) Src$^{-/-}$/Fyn$^{-/-}$/Yes$^{-/-}$ cells; and (B) Abl$^{-/-}$/Arg$^{-/-}$ cells.
Figure 2:
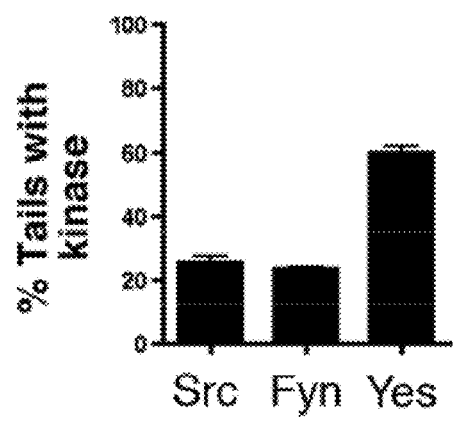

Notably, results indicated that VV retained the capacity to form actin tails in all these cell lines. No differences were apparent in the capacity to form actin tails in these cell lines compared to 3T3 cells derived from wild-type mice. In Src$^{-/-}$/Fyn$^{-/-}$/Yes$^{-/-}$ cells, the proportion of tails occupied by Arg or Abl was somewhat higher than that occupied by these kinases in wild-type cells. FIG. 2 provides a quantification the distribution of Abl- and Src-family kinases in VV actin tails in Src$^{-/-}$/Fyn$^{-/-}$/Yes$^{-/-}$ cells, or Abl$^{-/-}$/Arg$^{-/-}$ cells. In Abl$^{-/-}$/Arg$^{-/-}$ cells, the proportion of the tails occupied by c-Src was similar to that observed in wild-type cells, though that occupied by c-Fyn was lower, and that occupied by c-Yes higher compared to wild-type cells. In spite of the differences in distribution of kinases on the tails, these results suggest that neither c-Abl, c-Arg, c-Src, c-Fyn, nor c-Yes alone appears necessary for VV actin tail formation. Moreover, these results raise the possibility that other tyrosine kinases may also localize to actin tails, and/or that localization of kinases to actin tails may be a transient or sequential process.

The observations that Abl- and Src-family kinases localize in actin tails, that Abl-family kinases are activated, but that tails formed on cell lines derived from mice lacking members of either family suggest two alternatives. First, members of either family can catalyze actin tail formation, but in the absence of any one of these kinases, another Src- or Abl-family member can suffice ("functional redundancy"). Alternatively, localization and activation of Src- and Abl-family kinases could be unrelated to actin tail formation ("localized activation"). To determine whether redundant Abl- and Src-family kinases are involved in actin tail formation, a test of sufficiency was developed based on (i) the identification of inhibitors of tyrosine kinases that block actin tail formation in wild-type cells or cells lacking particular tyrosine kinases; and (ii) the capacity of kinase mutants resistant to such inhibitors to support actin tail formation with the inhibitor present.

Inhibitors of Src and Abl-Family Tyrosine Kinases Block Formation of Actin Tails.

To distinguish functional redundancy from localized activation, the effects of tyrosine kinase inhibitors in wild-type cells was first assessed. Pyrido[2,3-d]-pyrimidine (PD) compounds competitively inhibit binding of ATP to Abl-family kinases, including c-Abl and c-Arg, and kinases with homologous ATP-binding domains including c-Src, c-Fyn and c-Yes (Dorsey et al. (2000) Cancer Res., pp 3127-3131;

Kraker et al. (2000) *Biochem. Pharmacol.*, pp. 885-898; Wisniewski et al. (2002) *Cancer Res.*, pp. 4244-4255).

Figure 3:
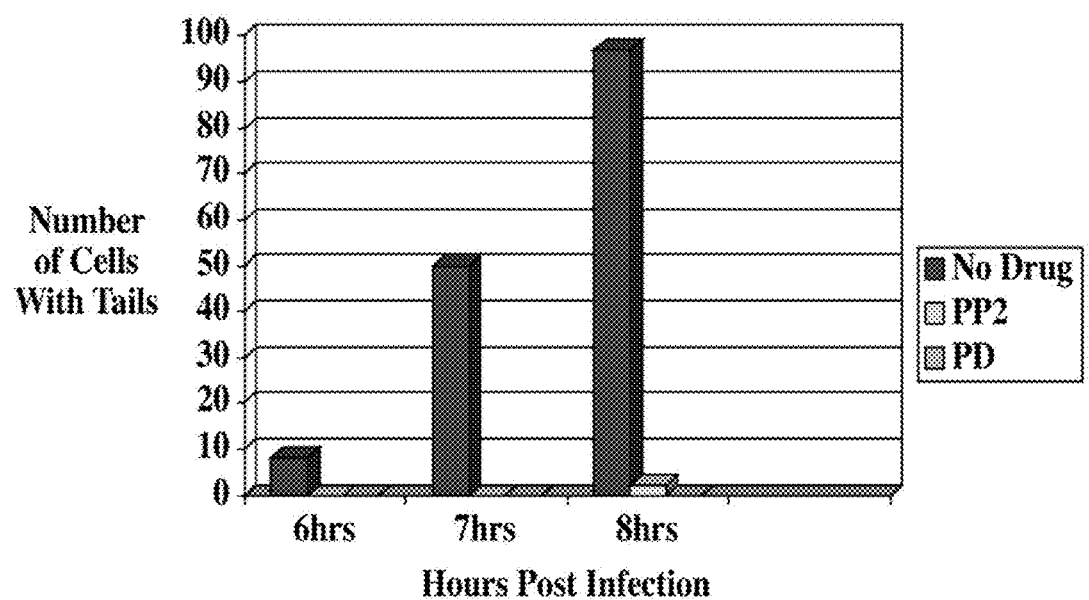
FIG. 3 shows a quantitation of the effect of treatment of 3T3 cells with Abl and Src-family kinase inhibitor PD166326 prior to exposure to VV for 8 hrs. Results reflect tails in 100 infected cells. Infection was assessed by EVP staining.

3T3 cells were treated with Abl- and Src-family tyrosine kinase inhibitor PD166326 (5 µM) and then exposed to VV for 8 hrs. Cells were stained with DAPI and α-phosphotyrosine pAb to recognize infected cells, and FITC-phalloidin to recognize actin. This condition resulted in the absence of actin tails. Likewise, in cells treated with 10 µM PD and then infected with VV, no actin tails were apparent. Concentrations of PD less than 1 µM were without effect. Staining with α-TW2.3, which recognizes a VV protein expressed early in infection (Yuwen et al. (1993) *Virology*, pp. 732-744), was evident in cells treated with 10 µM PD, suggesting that the drug did not block viral entry. Moreover, DAPI staining or staining with an α-phosphotyrosine pAb revealed the presence of extranuclear replication centers in the presence of 10 µM PD, indicating that the drug had no detectable effect on viral replication. Quantitation of the number of infected cells with actin tails showed that treatment with 10 µM PD reduced VV tail formation at each time point by at least 50 fold compared to the carrier control (0.1% DMSO; FIG. 3). Addition of 5 µM PD eight hours post infection for as little as 20 minutes also resulted in block of actin tail formation, though it is possible that PD additionally caused disassembly of extant actin tails. Compounds structurally related to PD (e.g. SKI-DV-1-10, 10 µM) were as effective as PD in blocking actin tails. The effects of PD were not due to non-specific inhibition of actin polymerization, as PD had no effect on the capacity of *Listeria monocytogenes* or *Shigella flexneri* to form actin comet tails.

PP2 and a structurally similar compound PP1 inhibit activity of Src-family kinases (Liu et al. (1999) *Chem. Biol.*, pp. 671-678) and have recently been recognized to additionally inhibit Abl-family kinases (Tatton et al. (2003). *J. Biol. Chem.*, pp. 4847-4853). Like PD, PP2 blocked actin tails at concentrations of 25 µM or greater, as reported previously (Frischknecht et al. (1999) *Nature*, pp. 926-929). In contrast to PD or PP2, STI-571, which inhibits Abl-family kinases but not Src-family kinases (Schindler et al. (2000) *Science*, pp. 1938-1942), did not block actin tail formation in wild-type 3T3 cells, even at concentrations as high as 25 µM.

PD Blocks Tyrosine Phosphorylation and Localization of Proteins Required for Actin Tail Formation.

It was next tested whether PD affects localization of phosphotyrosine staining and of Nck, N-WASP, or Arp2/3 complex at the tip of the actin tail. Phosphotyrosine staining as detected with the 4G10 mAb, colocalized with virions. Likewise, staining with α-Nck mAb, α-N-WASP pAb, α-Grb2 pAb and α-Arp p41 pAb was evident around the particle at the tip of the actin tail as reported previously (not shown). When 10 µM PD was added to cells infected 15 hrs previously with GFP-VV, no localization of phosphotyrosine with the virion as detected with 4G10 mAb. Likewise, no evidence was found for localization of Nck, N-WASP, or Arp2/3 localizing with the virion. The effect of PD on phosphotyrosine was selective for that associated with motile virions because phosphorylation of targets in the replication centers recognized by α-phosphotyrosine pAb was unaffected by addition of 10 µM PD. Together, these results demonstrate that PD blocks an essential tyrosine kinase activity associated with actin tail formation but not viral replication.

Several Abl- and Src-Family Kinases are Sufficient for VV Actin Motility.

It was next determined which Abl- and Src-family kinases are sufficient among PD-sensitive kinases for VV actin motility.

As noted above, STI-571 had no discernable effect on VV actin motility in wild-type 3T3 cells. However, addition of 10 µM STI-571 severely limited VV actin motility in cells lacking c-Src, c-Yes, and c-Fyn, reducing the number of average number of actin tails per cell by 16 fold to ~3 per cell on average with 30% of cells having none. STI-571 had no effect on viral replication, as evidenced by extranuclear DAPI staining, or on the transit of GFP-labeled virions to the cell periphery. Moreover, the carrier for STI571, DMSO, was without effect. Together, these data suggest that: 1) kinases sensitive to STI-571, which include c-Abl and c-Arg, are sufficient to support VV actin motility; and 2) of the kinases insensitive to STI-571, c-Src, c-Fyn, or c-Yes are likely the only ones capable of supporting VV actin motility in 3T3 cells.

To determine which among Abl- or Src-family kinases was sufficient for VV actin motility, it was next assessed whether c-Abl, c-Arg, or c-Yes could support VV actin motility in the absence of activity from other Src- or Abl-family kinases. In particular, expression of PD-resistant alleles of c-Abl, c-Arg, or c-Yes allowed actin motility to persist in the presence of PD was tested. Previous studies have shown that mutations within the ATP binding pocket (c-Abl-T315I, c-Arg-T314I and c-Yes-T348I) disrupt Van der Waals interaction between PD and the kinases, and increases the $K_i$ of PD from 10 nM to 1 µM as measured by in vitro kinase assay.

Next, it was tested whether these PD-resistant alleles of c-Arg or c-Abl could support VV actin tails when expressed in cells cultured in 10 µM PD. Actin tails were evident in PD-treated cells expressing YFP-c-Arg-T314I, but not in cells expressing endogenous c-Arg. Moreover, PD inhibited actin tail formation in cells overexpressing c-Arg-WT. Thus, buffering of PD, even by low affinity interactions with YFP-c-Arg-T314I, cannot account for the VV actin motility in this experiment. Not all PD-resistant tyrosine kinase alleles were capable of supporting actin tails in the presence of 10 µM PD.

In cells expressing c-Abl-T315I, actin tails were not observed in the presence of 10 µM PD. These results suggest that overexpressed tyrosine kinases, even ones that localize to the virion, do not cause nonspecific or aberrant phosphorylation of targets that support actin motility. Expression of the PD-resistant allele c-Yes-T348I, but not the wild-type allele, also supported actin tails in the presence of 10 µM PD. Together, these data indicate that c-Arg and c-Yes are sufficient among tyrosine kinases for VV actin motility, but do not rule out that other tyrosine kinases might also suffice. No evidence for the sufficiency of c-Abl in actin tail formation was found.

To determine whether other Src-family kinases were sufficient for VV actin motility, the effects of 10 µM STI-571 on cell lines lacking subsets of Src-family kinases were tested. Cells lacking c-Src and c-Yes, or cells lacking c-Fyn and c-Yes still supported VV actin motility in the presence of STI-571. Treatment with STI571 also had no detectable effects on the number of actin tails per cell. These results suggest that in addition to c-Arg and c-Yes, the Src-family kinases c-Src and c-Fyn are also sufficient for actin motility.

Redundant Src- and Abl-Family Kinases Mediate Cell-to-Cell Spread In Vitro.

To determine which tyrosine kinases participate in cell-to-cell spread, plaque assays were carried out on wild-type 3T3 cells or cells lacking various Src- and Abl-family tyrosine kinases. Infection of 3T3 cell monolayers with VV induces plaques within 4 days, though plaque morphology and size appeared somewhat more variable and less distinct than those seen upon infection of BSC-40 cells, a commonly used cell type. Nevertheless, plaques formed in the present experiment with equal efficacy on 3T3 cells, Abl$^{-/-}$ cells, Arg$^{-/-}$ cells, and Abl$^{-/-}$/Arg$^{-/-}$ cells, Src$^{-/-}$/Yes$^{-/-}$ cells, and Src$^{-/-}$/Fyn$^{-/-}$/Yes$^{-/-}$ cells.

To determine whether redundant tyrosine kinases mediate plaque formation, BSC-40 cells were treated with 10 µM PD, which blocks both Abl- and Src-family kinases. In accordance with a requirement of actin tails for cell-to-cell spread, PD reduced plaque size to "pinpoints," similar to those seen in VV A36R mutants which do not readily form plaques (Parkinson and Smith (1994) *Virology*, pp. 376-390). Identical results were obtained with 10 µM PD in 3T3 cells. However, STI-571, which only blocks Abl-family kinases, did not produce significant changes in plaque size or number in 3T3 cells or BSC-40 cells, though this compound did inhibit plaque formation in Src$^{-/-}$/Fyn$^{-/-}$/Yes$^{-/-}$ cells. Plaque reduction assays indicated that cells treated with 10 µM STI-571 or left untreated produced nearly equivalent amounts of virus after twenty-four hours, indicating that the drug had little if any detectable effect on viral replication. Together, these results provide evidence that the same redundant Abl- and Src-family kinases that mediate actin tail formation also mediate cell-to-cell spread as measured by plaque formation in vitro.

Abl-Family Kinases but not Src-Family Kinases Mediate EEV Release In Vitro.

To determine whether EEV formation in vitro was dependent on tyrosine kinases, wild-type 3T3 cells or 3T3 cells lacking various tyrosine kinases with VV were infected. Plaque assays of BSC-40 cells infected with supernatants derived from uninfected cells, VV-infected wild-type 3T3 cells, or 3T3 cells derived from animals lacking c-Src/c-Fyn/c-Yes, c-Abl, c-Arg, or c-Abl/c-Arg. Results indicated that plaques were present except when both c-Abl and c-Arg are absent, or when their activity is blocked with drug.

Supernatants were collected from cells 24 hrs after infection. At this time point, the supernatant contains plaque-forming units (PFU) composed of a significant amount of EEVs that have been released into the media (40-50%) and a contaminating IMVs release from lysed infected cells (Law and Smith (2001) *Virology*, pp. 132-142). The supernatant was then used to infect BSC-40 cells and plaque formation was assessed three days later.

Analysis of plaques on the BSC-40 cells indicated that supernatants from wild-type 3T3 cells, Src$^{-/-}$/Fyn$^{-/-}$/Yes$^{-/-}$ cells, Abl$^{-/-}$ cells, and Arg$^{-/-}$ cells all contained approximately the same PFU, but supernatants from Abl$^{-/-}$/Arg$^{-/-}$ cells contained 5-10 fold fewer PFU. Such a decrease could not be accounted for by lower infectivity of Abl$^{-/-}$/Arg$^{-/-}$ cells compared to wild-type cells because the same number of plaques formed on these cells as on wild-type cells, and viral growth obtained by lysing cells 24 hours after infection and measuring plaque forming units on BSC-40 cells revealed no differences between wild-type and Abl$^{-/-}$/Arg$^{-/-}$ cells. Together, these results suggest that for efficient EEV release, c-Abl or c-Arg are each sufficient, and that together they are necessary.

Next, the effects of inhibitors of Abl-family tyrosine kinases on EEV formation were assessed. BSC-40 cells were infected with VV and treated with 10 µM STI571 for 24 hours. The supernatent was then collected and used to infect BSC-40 cells and plaque formation was assessed three days later. Results for BSC-40 cells were identical to results obtained with supernatant from infected 3T3 cells left untreated or treated with the drugs. Application of 10 µM STI-571 caused a ~2-fold reduction in PFU on BSC-40 cells. Treatment of 3T3 cells or BSC-40 cells with STI-571 did not by itself affect plaque formation, nor viral replication measured by plaque reduction assays. Thus, the apparent reduction in EEV number caused by STI-571 could not be attributed to block of viral entry, inhibition of cell lysis, or to inhibition of replication. Consistent with an effect of STI-571 on formation of infectious EEVs, treatment of BSC-40 cells with 10 µM STI-571 also blocked the formation of "comets" apposed to plaques, a phenomena associated with EEVs. Finally, no difference in actin tail formation or number was evident in 3T3 cells treated with STI-571. Thus, the reduction in EEV number by STI-571 was not attributable to a decrease in the number of virions reaching the cell surface. Treatment of 3T3 cells with 10 µM PD likewise reduced the number of EEVs.

Given the possibility of IMV contamination in the cell supernatent, it was next confirmed that loss of Abl and Arg activity in the Abl$^{-/-}$/Arg$^{-/-}$ cells or with STI-571 treatment resulted only in a reduction of infectious EEVs and not in an additional effect on IMVs. To do this, supernatants were incubated with an antibody that neutralizes IMVs, called mAb 2d5. Addition of mAb 2d5 to supernatants reduced plaque number in both 3T3 and BSC-40 cells by ~40% in agreement with previous reports (Law and Smith (2001) *Virology*, pp. 132-142). Second, addition of 10 µM STI-571 caused the same fold reduction in plaque number in the presence or absence of mAb 2D5, and the percentage reduction in plaque number with STI-571 treatment or in Abl$^{-/-}$/Arg$^{-/-}$ cells was similar irrespective of the addition of mAb 2d5. Together these data suggest that Abl and Arg have little effect on IMVs, and that c-Abl and c-Arg, but not Src-family kinases, mediate release of EEVs from infected cells in vitro.

STI-571 Reduces VV Load in Mice.

To determine the role of tyrosine kinases in EEV formation and virulence in vivo, the effects of STI-571 on viral load in mice infected with VV was examined. STI-571 (100 mg/kg/day dissolved in 0.9% sterile saline) or the saline carrier was delivered to mice via Azlet osmotic pumps placed subcutaneously. Twenty-four hours after insertion of the pump, some of the mice were innoculated with $10^4$ pfu VV intraperitoneally. The remaining mice were left untreated. Four days post infection mice were sacrificed, and the ovaries were extracted and subjected to real time PCR to evaluate viral load. Ovaries were chosen for analysis because this organ, together with cervical tissue, have been found to contain the highest levels of virus following intraperitoneal infection (Ramirez et al. (2003) *Arch. Virol.*, pp. 827-839).

Figure 4:
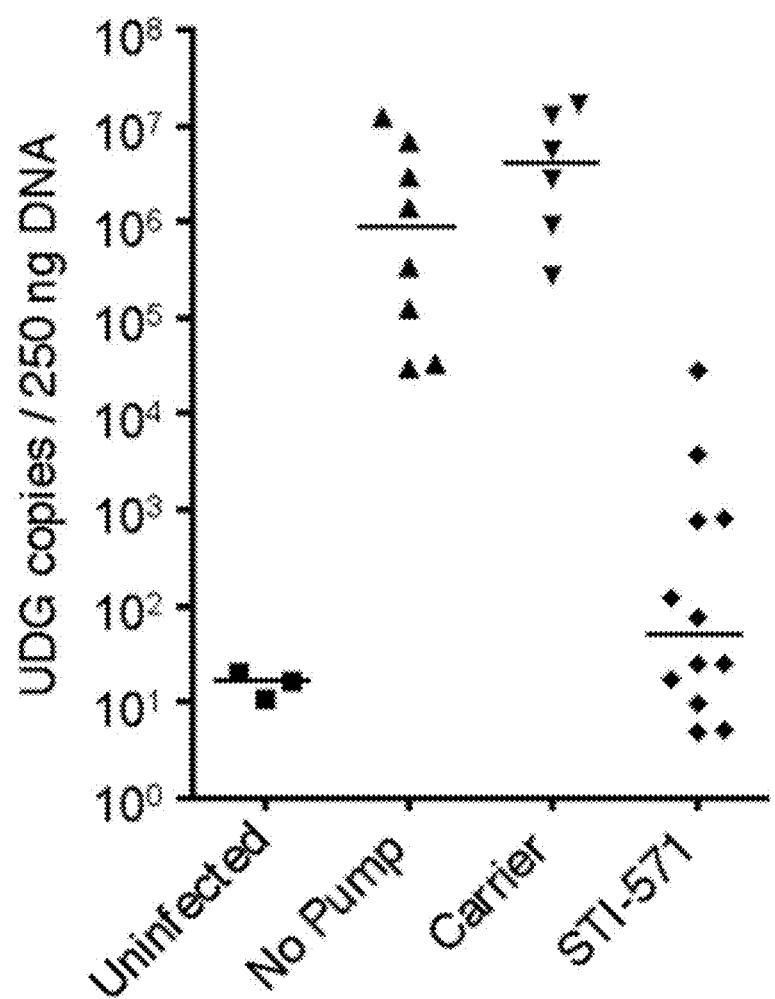
FIG. 4 shows that STI-571 reduces VV load in mice. Six week-old C57/B6 mice were left uninfected (no virus), or infected with $10^4$ PFU/ml VV. One day prior to infection, continuous release osmotic pumps containing PBS (carrier) or STI-571 (100 mg/kg/day) were surgically implanted subcutaneously. The line in each data set represents the median viral load. The data are significant ($P<10^{-6}$) by Fisher's exact test.
Figure 5:
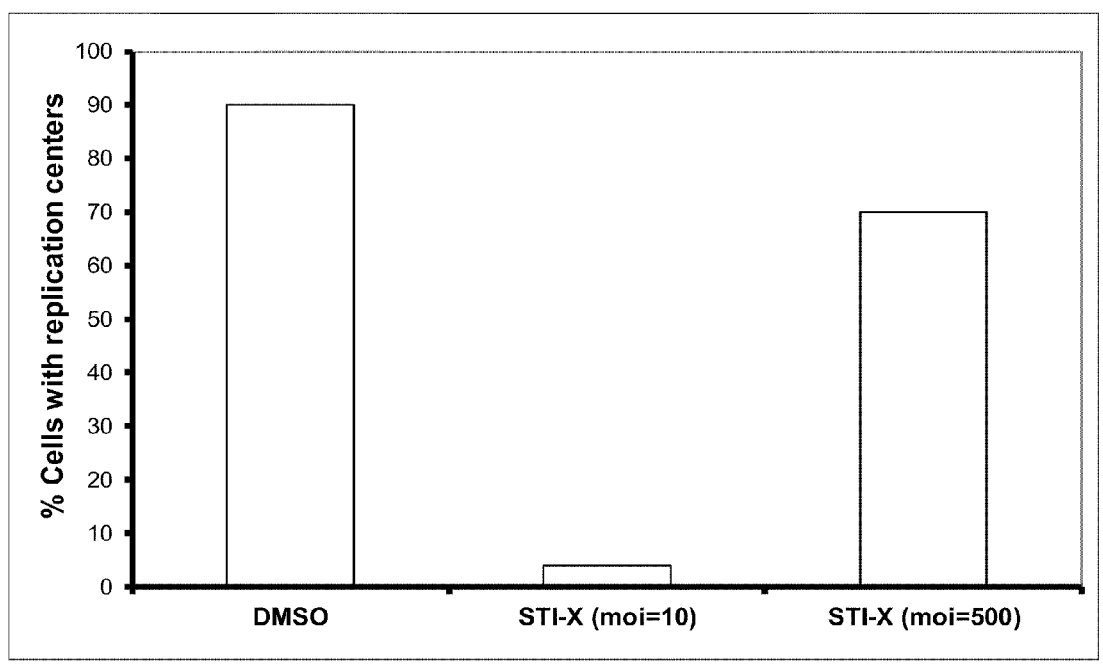
FIG. 5 shows quantitation of the effects of STI-X on viral replication. The percentage of infected cells is plotted, assessed by either EVP staining or the presence of GFP-labeled virions that contained extranuclear replication centers, as measured by extranuclear DAPI staining.

Viral load was measured as the number of copies of the VV UDG gene per 250 ng of DNA isolated from an ovary. In untreated animals or animals with pumps containing saline carrier, significant levels of virus were detectable in the ovaries (~$10^7$ copies/250 ng DNA), indicating spread of the virus to organs adjacent to the peritoneal cavity. The detection limit of the assay, determined by serial dilution, was 10 viral genomes. Treatment with 100 mg/kg/day STI-571, a concentration used in mouse leukemia models (Wolff and Ilaria, 2001), reduced viral load by 4-5 logs (FIG. 4). This difference was judged statistically significant by a two-sided Fisher's exact test ($P<10^{-6}$; see Methods).

Conclusions

The results described above demonstrate that tyrosine kinases are participants in motility, release, and pathogenic infection of Vaccinia virus. In particular, Abl-family kinases, but not Src-family kinases, are required for efficient actin motility, and tyrosine kinase inhibitors that inhibit Abl-family kinases, including PD compounds, block actin motility. PD compounds and STI-571 block release of infectious virions, and STI-571 reduces viral load in VV-infected mice. In this regard, these results indicate that drugs such as PD and STI-571 are useful for the prevention or treatment of VV infection.

Because Vaccinia and variola viruses are similar, it is likely that these drugs would also have increased efficacy against variola infections in humans that cause smallpox.

Experiment 2

STI-X Inhibits Vaccinia Replication

This experiment involved screening a small library of compounds relating to STI-571 to identify a compound affecting VV replication. A derivative of STI-571, named STI-X, was identified and examined for its effect on VV infection, replication, and motility.

Methods

Methods for cell culture and fluorescence microscopy-based plaque assays were similar to those as described in Experiment 1.

In an effort to identify compounds that affect VV replication, a library of STI-571 derivatives was constructed by making modifications to particular moieties on the molecule. These compounds were screened based upon their ability to inhibit the infection of 3T3 cells, assessed by either EVP staining or the presence of GFP-labeled virions that contained extranuclear replication centers, as measured by extranuclear DAPI staining.

3T3 cells were left untreated, or incubated with 1 μM STI-X or DMSO, the carrier. Cells were then infected with GFP-VV at an moi of 10 for 8 hours. STI-X was added at the time of infection or 6 hrs after. Eight hours after infection, cells were fixed and stained with DAPI α-Ptyr-Cy5 pAb to recognize replication centers, Cy3-phalloidin to recognize actin comet tails.

Results

The presence of GFP-virions was noted in infected cells and extranuclear replication centers absent. Ptyr staining was also absent, and no actin tails were evident. Punctate extranuclear DAPI staining that corresponded to the GFP-WR virions that initially infected the cell was evident. When STI-X was added after replication centers had formed, replication centers, and actin tails were still evident.

EVP staining and DAPI-stained extranuclear "replication factories" were evident in all untreated and DMSO-treated cells, and 90% of these cells contained actin tails, indicating that the infection was robust. GFP-labeled virions and EVP staining were also evident in all STI-X-treated cells, indicating that STI-X had little detectable effect on viral entry. However, STI-X treatment caused a marked decrease in the percentage of cells containing DAPI-stained extranuclear viral replication factories compared to DMSO or untreated cells (100% for untreated cells compared to 4% for STI-X; FIG. 2). In GFP-WR-infected cells, punctate extranuclear DAPI staining was barely visible (e.g. FIG. 8A). Because the staining colocalized with GFP-WR virions, the DNA likely corresponded to virions that initially infected the cell.

STI-X-treated cells also failed to form actin tails, presumably because replication was inhibited. To test this directly, STI-X was added after replication centers had formed. Under these conditions, STI-X had no effect on replication centers (as measured by DAPI staining or α-Ptyr pAb) nor on actin motility.

Plaque assays and plaque reduction assays confirmed these microscopy observations. Plaque formation was reduced in the presence of STI-X, though the drug proved less effective when the moi was increased, a common property of antiviral drugs. The plaque assays, which were carried out over three days, indicate that the drug was well tolerated over that time period (even up to 8 days, the longest time assessed). In plaque reduction assays, the cells were infected for 24 hours in the presence or absence of STI-X. The VV was then recovered by liquid Nitrogen lysis, and the titer assessed by plaque assay in the absence of drug.

Conclusions

In summary, STI-X blocks VV replication and is useful for the prevention or treatment of VV infection.

Experiment 3

Effect of STI-X, PD, and Combination Treatment on Aspects of VV and Variola Infection This experiment is designed to determine the efficacy of PD, STI-X, or a combination of the two in reducing or minimizing pathogenicity in VV or Variola infected mice. C57 BL/6 mice are used for these studies. Mice are infected in a BSL2 facility to prevent infection of other mice.

STI-X and PD on VV and variola infection. Intradermal inoculation of mice with VV has been proposed to model VV vaccination in humans (Tscharke et al. (1999) *J. Gen. Virol.*, 80: 2751-5; Tscharke et al. (2002) *J. Gen. Virol.*, 83: 1977-86). Using this model, it has been shown that intradermal inoculation on the ears of 6 week-old C57BL/6 mice with VV strain WR produces 3 mm lesions within 8 days. The lesion disappears after about three weeks indicating that the animal has developed an immune response and cleared the infection. This model was developed based on experimental groups of 5, female, age matched 6 week old C57BL/6 mice infected with $10^4$ pfu intradermally on the ear, with lesion diameter measured daily over a three week time course. The present experiment follows this paradigm.

Intranasal inoculation of mice with VV has been proposed to model the normal path of variola inoculation in humans. Intranasal VV infection at an moi of $10^3$ to $10^6$ of 8 week old female BALB/c mice leads to dramatic weight loss, reduced activity, and ultimately death within 10 days (Reading et al. (2003) *J. Immunol.*, 170: 1435-1442).

The effect of PD or STI-X administered alone on lesion size (for intradermal inoculation) or mortality (for intranasal inoculation) in VV WR-infected mice is assessed. Half the mice are treated with PD or STI-X (administered via pump), and the control mice are treated equally with PBS or the drug formulation. Initially, the highest dose of PD or STI-X achievable without toxic effects is used. For mice inoculated intradermally, lesion size is measured daily. For mice infected intranasally, weight is measured daily.

At day 10 mice are sacrificed and brains and lungs are harvested. Mice losing greater than 30% of their body weight are sacrificed immediately. Tissues are frozen and thawed tree times and sonicated, and the viral titre determined by plaque assay on 3T3 cells (Reading et al. (2003) *J. Immunol.*, 170: 1435-1442). Data are analyzed statistically by the nonparametric Mann-Whitney t test, and if PD or STI-treated mice harbor significantly different plaque forming units compared to control mice ($p<0.01$) then it is concluded that the drug influences viral burden in infected mice. To rule out the possibility that viral invasion and proliferation is blocked by the drug formulation, or by some non-specific means, the effects of the formulation alone will be measured.

To assess the health of mice inoculated intranasally, appearance of mice are graded by a blinded observer: one point is assigned to each condition: listlessness, ruffled coat, (maximum score=2; minimum score (robust health)=0). In addition, body weight results are expressed as average values +/− one standard error. Treatment groups include at least five mice. Statistical analysis is calculated by the Mann-Whitney t test, with p<0.01 considered significant. If drug treated groups yield reduced pathology scores, it is concluded that PD therapy positively affects VV disease outcome.

Combined Administration.

This study assesses whether PD and STI-X administered together have the potential to provide better protection against intranasal or intradermal VV infection than either drug alone. A formulation compatible with both drugs is determined and the drug combination delivered via an Alzet pump to infect the animal intranasally or intradermally. Differences in lesion size or survivability compared to either drug administered alone or no drug are determined and analyzed as described above. Variation of the drug concentrations are required if the combination proves toxic.

Assessment of Acquisition of Immunity to VV.

This study assesses whether STI-X or PD treatment allows effective vaccination. The drug or the carrier is administered via inoculation as described above. When the animal recovers and drug delivery has been discontinued, the animal is reinoculated. Inoculation is carried out either intradermally and the size of the ensuing scab determined, or intranasally at a dose lethal to animals not previously exposed to the virus. Scar size or mortality rates are assessed and are similar to animals not previously exposed if PD or STI-X interfere with acquisition of immunity. Alternatively, measurement of serum titres against known VV proteins and carefully dosing the drugs to avoid complications can be utilized.

Reduction of Infectivity in Immunocompromised Patients.

This study assesses whether STI-X and PD are useful in limiting VV disease in immunocompromised individuals. $Rag1^{-/-}/Rag2^{-/-}$ mice have no capacity to mount an adaptive immune response and develop severe infections. Whether intradermal inoculation with VV produces a more severe disease in these animals compared to matched wild-type animals is assessed. If so, whether administration of STI-X or PD alone or in combination serves to protect the animal from a more severe infection will be analyzed.

Experiment 4

Entoropathogenic *E. coli* and Enteroheammorhagic *E. coli* Act Through Abl Family Tyrosine Kinases to Form Actin Pedestals Methods 3T3 cells were grown on glass coverslips in Dulbecco Modified Eagles media (DMEM) supplemented with 10% Fetal Calf Serum and incubated for six to eight hours at 37° C. with WT EPEC (strain 2389/69) at an m.o.i. of 10, or EHEC EDL933 or EHEC-LiSTX at a m.o.i. of 40. For some experiments, cells were transfected three days prior to infection with plasmid vectors using Fugene-6 (Boehringer).

Cells were processed for immunofluorescence or Western analysis. EPEC was recognized by staining with 4'6-diamidino-2-phenylindole (DAPI; 1 μg/ml; Sigma), and pedestals were recognized by staining with FITC-phalloidin (1 μg/ml; Molecular Probes). Before staining, some pAbs were incubated for twenty minutes with EPEC or EPEC-Δ-Tir previously fixed in formaldehyde, and then centrifuged. This procedure removed serum contaminants that nonspecifically bound EPEC.

The primary antibodies and concentrations used in this study were as follows: α-WASP pAb (affinity purified, 1:200 dilution), α-hemagglutinin A (HA) mAb (3F10; 0.01 μg/ml; Roche Diagnostics), α-Nck mAb (1 μg/ml; Oncogene Science, Cambridge, Mass.), α-Abl mAb (AB3; 0.5 μg/ml for overexpressed Abl proteins; 50 μg/ml for endogenous Abl proteins; 8E9; 0.05 μg/ml; BD PharMingen, San Diego, Calif.), α-Tir pAb (1:2000 for microscopy; 1:50,000 for Western analysis; from Jim Kaper, University of Maryland, College Park, Md.), and α-Src pAb (0.1 μg/ml; Santa Cruz Biotechnology, Santa Cruz, Calif.), and α-Abl-pY412 and α-Abl-pY245 pAbs (0.1 μg/ml; Cell Signaling Technology, Beverly, Mass.). Cells expressing exogenous c-Abl-WT were distinguished by relatively high fluorescence intensity with lower α-Abl mAb concentrations. Thus, images were acquired with much shorter exposures than those used to detect endogenous c-Abl-like protein. Secondary antibodies were obtained from Jackson ImmunoResearch Laboratories (West Grove, Pa.).

PD compounds PD166326 and SKI-DRV-1-10 were synthesized as described elsewhere herein and were indistinguishable in their effects in all assays. PD compounds and PP2 were dissolved in 100% DMSO. For pretreatment experiments, PD, PP2, or DMSO was added to cells one hour prior to infection with bacteria. For "reversal" experiments, compounds or DMSO were added to cells five hours after addition of bacteria, and the cells fixed two hours subsequently.

Images were acquired with a scientific-grade cooled charge-coupled device on a multi-wavelength wide-field three-dimensional microscopy system (Intelligent Imaging Innovations). Immunofluorescent samples were imaged in successive 0.25 μm focal planes through the samples, and out-of-focus light was removed with a constrained iterative deconvolution algorithm. To quantitate the effects of PD and PP2, it was noted that pedestals stained more intensely with FITC-phalloidin than actin filaments. Images were segmented on the basis of intensity. The correspondence of the highest intensity pixels to pedestals was confirmed visually. Cases where high pixel intensity and pedestals failed to coincide were adjusted accordingly. The area occupied by the highest intensity pixels was then calculated. For each condition, data were acquired from cells plated and infected identically on the same day. Each experiment was repeated five times. Some variance in maximal pedestal area was evident between experiments due to variation in plating density and infection efficiency.

Results

Transfected c-Abl and Endogenous Proteins Reembling Abl Localize in Actin Pedestals.

Because phosphorylation of EPEC Tir triggers the pathogenic program in the host, this experiment set out to identify the tyrosine kinase involved in this process. To determine whether endogenous proteins resembling Abl localized within pedestals, 3T3 cells were exposed to EPEC or EHEC, and then stained with α-Abl monoclonal antibody (mAb) AB3 that recognizes an undefined epitope in the C-terminus. Pedestals were seen as intense actin staining, directly apposed to the bacterium. An endogenous protein recognized by α-AbI-AB3 mAb was enriched in pedestals relative to the cytoplasm. Identical results were obtained with α-Abl-8E9 mAb, which recognizes a kinase domain epitope in both EPEC and EHEC pedestals. Exogenously expressed haemagglutinin A (HA)-tagged Abl (HA-Abl), detected with the α-HA-3F10 mAb, also localized in EPEC and EHEC pedestals. The localization of Abl-like protein in pedestals was specific: neither endogenous nor exogenous Src-like protein, detected with α-Src pAb, nor green fluorescent protein fluorescence were enriched in EPEC or EHEC pedestals relative to the cytoplasm.

To determine whether endogenous proteins sharing common epitopes with Abl localized in the pedestals, 3T3 cells derived from mice lacking both Abl and the Abl-related kinase Arg were infected. Both EPEC and EHEC were still capable of forming pedestals in Abl$^{-/-}$/Arg$^{-/-}$ cells, and a protein recognized by α-Abl-AB3 but not by α-Abl-8B9, was evident beneath the bacterium. Together these results suggested that although Abl localizes in pedestals, other antigenically related proteins are also present.

PD Compounds that Block Abl and Related Kinases Block and Reverse Pedestal Formation.

It was next determined whether Abl or Abl-like proteins were required for pedestal formation initiated by EPEC or EHEC. Because Ab$^{-/-}$/Arg$^{-/-}$/cells can form pedestals. An approach was chosen that would target both Abl and structurally related proteins. Pyrido[2,3-d]pyrimidine (PD) compounds competitively inhibit binding of ATP to Abl and kinases with homologous ATP-binding domains, and are being developed to treat cancers caused by dysregulated Abl (e.g. CML). With PD treatment, few attached EPEC or EHEC were evident, and little or no actin was apparent beneath bacterium that did attach, even with extended incubations (up to 8 hrs). Concentrations of PD less than 5 μM were without effect.

Figure 6:
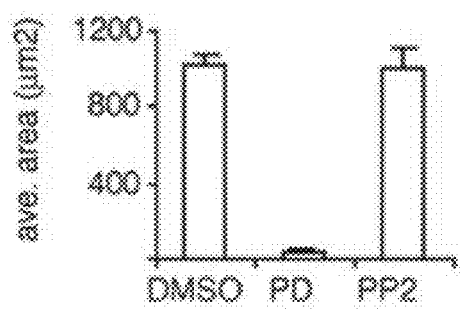
FIG. 6 shows that the formation and maintenance of EPEC pedestals is blocked by PD166326 and related kinase inhibitors. Graphs show the area occupied by the highest intensity pixels for EPEC treated according to the pretreatment or reversal regimens with DMSO, 10 µM PD166326, or 10 µM PP2. EPEC were cultured with either 0.1% DMSO (X) or 25 µM PD (Δ) and the OD 600 measured at the times indicated.
Figure 6:
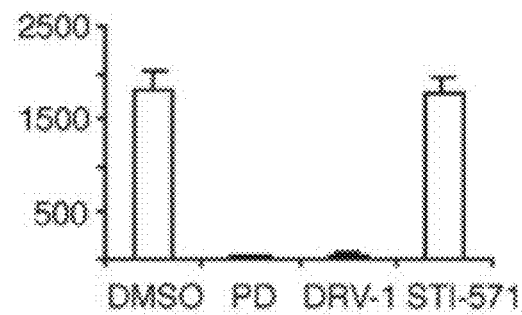
Figure 6:
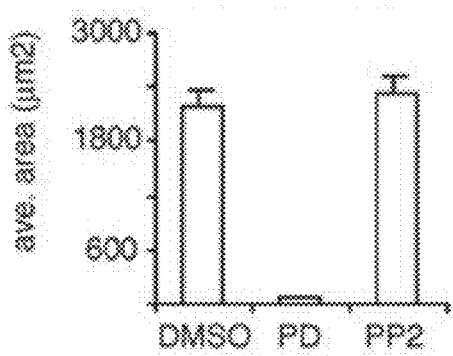
Figure 6:
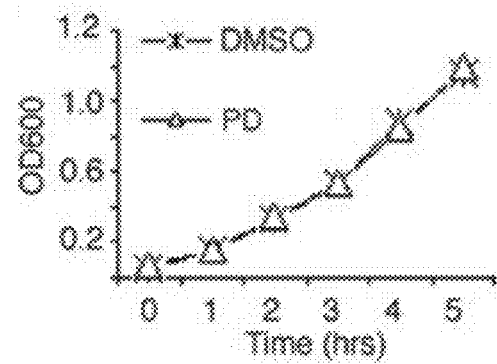

Quantitation of pedestals showed that PD treatment reduced EPEC and EHEC pedestal formation by 50 fold (FIG. 6). FIG. 6 shows area occupied by the highest intensity pixels for EPEC treated according to the pretreatment or reversal regimens with DMSO, 10 μM PD166326, or 10 μM PP2. PD analogs (SKI-DV-1-10 [DRV-1]; 10 μM) blocked EPEC pedestal formation but STI-571 (25 μM) did not. Growth of EPEC was unaffected by treatment with PD166326. EPEC were cultured with either 0.1% DMSO (X) or 25 μM PD (A) and the OD 600 measured at the times indicated.

Because PD compounds also inhibit some Src-family kinases, the effects of PP2, which inhibits Src-family kinases but not Abl-related kinases, was tested. PP2 at concentrations up to 100 μM, the highest tested, or the carrier DMSO (0.1%) were without effect. To test for functional redundancy between Abl and Src or other kinases, the effects of the inhibitors in Abl$^{-/-}$/Arg$^{-/-}$ cells was assessed. As in wild-type cells, PD but not PP2 inhibited pedestals were examined. The absence of pedestals was not attributable to a bactericidal effect of PD because no effect on growth or viability of EPEC or EHEC was apparent. The effects of PD were also not due to non-specific inhibition of actin polymerization: PD had no effect on the capacity of *Listeria monocytogenes* to attach, invade, or form actin comet tails. Together, these data indicate that Abl or-functionally redundant kinases that are sensitive to PD mediate pedestal formation.

It was next tested whether PD affected localization of Tir, Nck, N-WASP, or the Arp2/3 complex beneath attached EPEC and EHEC. Tir localized in the pedestal beneath attached bacterium, and was detectable by Western analysis after 3 or more hours of infection. With PD treatment, Tir protein remained detectable beneath attached EPEC or EHEC, despite the absence of pedestals. Although Nck, N-WASP, and Arp2/3 complex are required for EPEC pedestal formation and, like Tir, localize in the pedestal, recruitment of Nck, N-WASP, and the Arp2/3 complex beneath EPEC was blocked by PD.

Tir Phosphorylation is Blocked and Reversed by PD Compounds.

Figure 7:
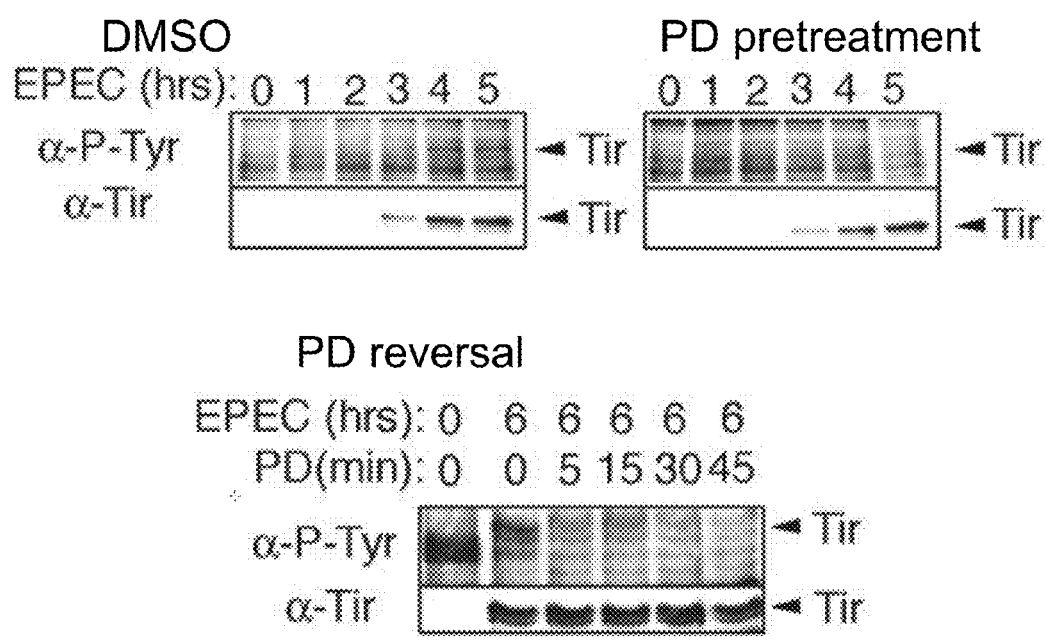
FIG. 7 shows that PD blocks tyrosine phosphorylation of EPEC Tir but not Tir localization. Cells were treated with DMSO or PD and were left uninfected (0 h) or infected with EPEC for the times indicated. For the reversal condition, cells were left uninfected (lane 1) or infected with EPEC for 6 h, treated with PD for the times indicated, and analyzed.

Because pedestal formation and recruitment of Nck, N-WASP, and Arp2/3 depend on Tir phosphorylated at Y474, it was next determined whether PD affected Tir phosphorylation. As shown in FIG. 7, cells were treated with DMSO or PD and were left uninfected (0 h) or infected with EPEC for the times indicated. Cells were lysed and subjected to Western analysis with α-phosphotyrosine in Ab 4G10, stripped, and then reprobed with α-Tir pAb. Note that Tir protein is evident after 3 h and becomes phosphorylated in DMSO-treated cells and that PD blocks Tir phosphorylation. For the reversal condition, cells were left uninfected (lane 1) or infected with EPEC for 6 h, treated with PD for the times indicated, and analyzed. Note the band corresponding to Tir becomes dephosphorylated within 5 min of adding PD.

These results suggest that PD blocks EPEC pedestal formation by blocking Tir phosphorylation, and, as a consequence, recruitment of distal signaling molecules such as Nck, N-WASP, and Arp2/3 complex that are required for actin polymerization. PD may also affect the capacity of these molecules to localize.

Abl is Sufficient for Tir Phosphorylation and Pedestal Formation in the Absence of Other Able-Related Kinases.

Localization of Abl within pedestals suggested a role in Tir phosphorylation and actin polymerization, but the observation that Abl$^{-/-}$/Arg$^{-/-}$ cells permit pedestal formation, and the broad substrate specificity of PD suggest that other kinases might also participate. It was next determined whether Abl kinase was sufficient among PD-sensitive kinases for tyrosine phosphorylation or pedestal formation. This study took advantage of a mutation in BCR-Abl (T3151) acquired by CML patients, which renders the protein resistant to inhibition by ST1-571 or PD. The T3151 mutation was engineered into c-Abl (cAb1-3151). Expression of cAbl-T3151 in cells cultured in PD, restored EPEC and EHEC pedestal formation, as well as localization of phosphotyrosine beneath attached bacterium. Expression of c-Abl-T3151 also prevented loss of tyrosine phosphorylation in the pedestal when PD was added after pedestals had formed. Overexpression of c-Abl, even at high levels, was not sufficient to restore pedestal formation in PD, nor block loss of phosphorylation induced by PD, suggesting that the effects of c-Abl-T3151 were due to its kinase activity rather than to low affinity binding and titration of PD.

Known Substrates of Abl or Abl-Related Kinases Localize in EPEC and EHEC Pedestals.

To test whether EPEC Tir is a substrate for Abl, Tir was immunoprecipitated from cells previously infected with EPEC under conditions where Tir became dephosphorylated during isolation. The presence of Tir was assessed by Western blotting with α-Tir pAb, and phosphotyrosine detected with 4G10 mAb. Addition of ATP together with purified Abl kinase to immunoprecipitated Tir resulted in tyrosine phosphorylation of Tir, and addition of PD blocked Tir phosphorylation. Whether the tyrosine phosphorylated site on Tir resembled that found in Abl targets was also assessed. CrkII is phosphorylated by Abl at Y221 and pAbs that recognize the phosphorylated Y221 on CrkII also recognize phosphorylated Tir. Thus, Abl is capable of directly phosphorylating EPEC Tir in vitro, and the phosphorylated site on Tir resembles that found in. a known Abl substrate.

Conclusions

Together, these results suggest that c-Abl activity is, among tyrosine kinases, sufficient for pedestal formation initiated by EPEC or EHEC and of EPEC Tir phosphorylation. Results with Abl$^{-/-}$/Arg$^{-/-}$ cells suggests that other tyrosine kinases that are sensitive to PD, and which share with c-Abl the capacity to localize in pedestals and to phosphorylate Tir or other pedestal proteins, may also suffice. Indeed, functional redundancy among tyrosine kinases is well recognized even among Abl-family members. These studies provided the first results identifying a role for tyrosine phosphorylation in EHEC pedestal formation and the first description of any tyrosine kinase sufficient for either EPEC or EHEC signalling. These results indicate that PD or related compounds may be useful to treat or prevent EPEC and EHEC infections.

Experiment 5

C. rodentium is a Useful Model of EPEC

To determine whether C. rodentium infection in mice is a useful model of EPEC infection in humans, the question of whether C. rodentium causes pedestal formation by the same mechanism as EPEC. It was found that Tir, phosphotyrosine, Nck, N-WASP, Abl, and the Arp2/3 complex all localize within C. rodentium pedestals. Moreover C. rodentium failed to form pedestals on fibroblasts derived from N-WASP-deficient mice. It was next determined whether C. rodentium pedestals were sensitive to PD. PD in fact blocked and "reversed" C. rodentium pedestals. Together these results suggest that pedestals induced by EPEC and C. rodentium form by the same mechanism and are blocked and reversed by PD.

Experiment 6

Administration and Detection of Drugs in Mice

To test the efficacy of the compounds of the present invention in mice, a means of introducing PD and STI into mice and detecting the compounds in serum was developed. In addition, the LD90 for VV in vivo was determined.

Figure 8:
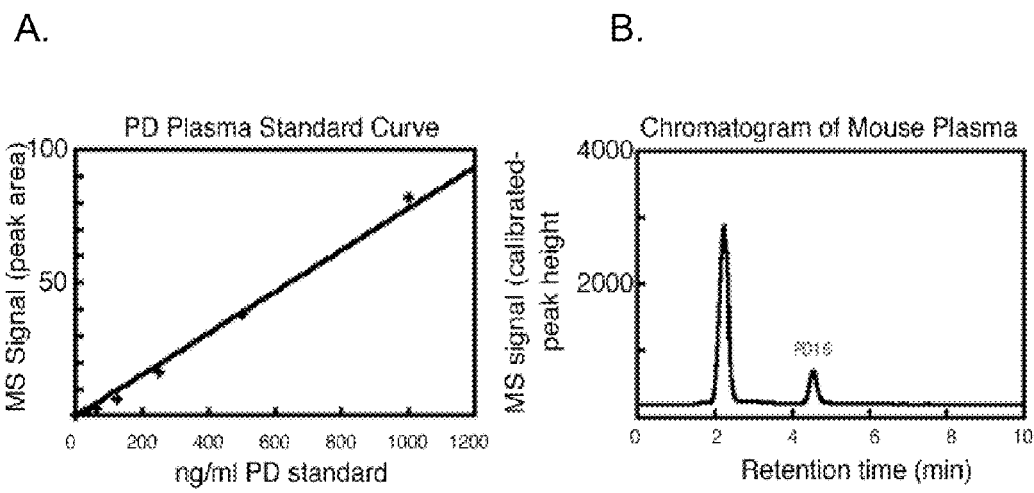
FIG. 8(A) shows the standard plasma curve for PD is linear from 1000 to 30 ng/ml.
FIG. 8(B) shows a chromatogram of mouse plasma. The mass spectroscopy readout is plotted as function of the retention time on the column. The first peak is an internal calibration standard and the second is PD.

Intranasal inoculation with 20 μl $10^4$ pfu/ml VV strain WR kills ~100% of mice within 6 days, whereas 20 μl $10^3$ pfu/ml killed ~50% of the mice, in general agreement with published reports (Reading et al. (2003) J. Immunol., 170: 1435). Intraperitoneal injection with up to 100 mg/kg/day STI-571 (in saline) or up to 30 mg/kg/day PD-166326 (in 31% PEG400/31% DMSO/38% Saline) was well tolerated in mice for up to 10 days, the longest time tested. For STI-571, the dose was 10 fold higher than that used to treat CML in humans, but was chosen based on the capacity of the animals to tolerate the compound, which they did (Druker et al. (2001) Chronic myelogenous leukemia. Hematology (Am Soc. Hematol. Educ. Program): 87; Wolff and Ilaria (2001) Blood, 98: 2808). Drug levels can easily be titrated to determine the minimum amount required. With drug alone, mice showed no indication of weight loss over the 10 day period, and had no overt pathology upon necropsy. Using HPLC/Mass spectroscopy it has been possible to detect PD in the serum of injected animals at concentrations as low as 30 ng/ml. The standard curve for PD is linear from 1000 to 30 ng/ml (FIG. 8A). The sample volume required is 30 μl. PD was detected based on molecular weight (ion current).

The plasma sample was subjected to solid phase extraction to concentrate PD and remove plasma proteins, eluted on a Zorbax Stable Bond C8 column, and monitored in the MS (APCI positive SIM at 427). The MS readout is plotted as function of the retention time on the column. The first peak is an internal calibration standard and the second is PD (FIG. 8B).

To quantitate viral load in infected mice, a real-time PCR assay was utilized to detect as few as 7 copies of VV in tissue samples. Ovaries or brains and other organs were digested with proteinase K, and the DNA extracted and purified (Qiagen). The DNA content was normalized, and equivalent amounts of DNA were subjected to real time PCR (1-cycler) with VV WR-specific primers and a Taqman/FAM dye/quencher system. The amount of DNA in the sample was calibrated with known VV DNA standards. Using this method, the viral load in mice treated with STI-571 was 6 orders of magnitude lower than that seen in untreated mice.

Experiment 7

C. elegans Screens Define Novel Drug Targets in the Host

Studies on EPEC and EHEC pathogenesis are limited by an extremely complex genome, comprising 1387 gains and 528 losses compared to E. coli K12, and by a lack of functional assays for many of the proposed virulence factors (Perna et al. (1998) Infect. Immun. 66: 3810). Here, a means was identified by which EPEC and EHEC pathogenesis may be studied in the nematode C. elegans: under specific growth conditions, the bacteria killed the worms. The killing is relevant to human disease because bacterial mutants that are nonpathogenic in humans also do not kill worms.

In a screen of mutant worms known to confer resistance to killing with other microbes, it was found that the daf-2 gene, which prolongs the lifespan of C. elegans, conferred resistance to killing by EPEC and EHEC (Dorman et al. (1995) Genetics, 141: 1399; Murphy et al. (2003) Nature, 424: 277). This is the first demonstrated genetic system available for studying EPEC or EHEC pathogenesis. Because both organisms can be genetically manipulated, this system offers the capacity to identify and characterize mutants in both host and pathogen. This system will allow studies on EPEC and EHEC pathogenesis in C. elegans that may yield identification of novel bacterial virulence factors and targets of such factors in nematode and mammalian hosts.

Experiment 8

PD Blocks Polyoma Virus Replication In Vitro

The polyoma virus protein Middle T (MT) is essential for the virus to mount a high-level productive infection, to transform cells in vitro, and to generate tumors in susceptible strains of mice. MT is a type II integral membrane protein that recruits, binds, and activates the host cell kinases c-Src, c-Fyn, and c-Yes. A number of in vitro and in vivo studies have established that the capacity of MT to bind and activate these tyrosine kinases is required for the viral growth promoting and oncogenic functions. Virtually all humans are persistently infected with each of the two known human polyomaviruses: JCV and BKV.

Although human polyoma viruses do not encode an MT protein, a homologous protein small T (ST) does exist. Other viruses, such as EBV, also target Src kinase (Longnecker et al. (1991) J. Virol. 65: 3681).

In this experiment, the effect of PD and STI-571 on the cytopathic effects of Polyoma virus on 3T3 cells was assessed. Both PD and STI-571 inhibited cytopathic effects. Monolayers of 3T3 cells were left uninfected or infected for 5 days with Polyoma virus. Cells in the infected group were divided into conditions: DMSO (the carrier for PD); 10 μM STI-571; and 1 μM PD166326. Polyoma infection caused cell death in the DMSO group, but addition of STI-571 and PD reduced the extent of killing. These results demonstrate that these compounds are therefore useful as inhibitors of Polyoma virus infection.

Experiment 9

STI-571 Blocks HIV Replication In Vitro

The present experiment examined the effect of STI-571 on HIV replication. Culture macrophages were infected with either media, HIV-Bal, various dosages of STI-571, or various dosages of STI-571 combined with HIV-1 Bal. Viral replication (measured by p24 levels) was reduced by up to 4 fold in a dose dependent fashion by addition of STI-571 (Table 1). These results demonstrate that STI-571 is useful as an inhibitor of HIV infection.

TABLE 1

Effects of STI-571 on p24 production 7 and 14 days after infection of macrophages with HIV-1 Bal.

| Culture Condition | P24(pg/ml) day 7 | P24(pg/ml) day 14 |
|---|---|---|
| Cells + media | <10 | <10 |
| Cells + HIV-1 Bal | 322 +/− 28 | 956 +/− 34 |
| Cells + STI-571 1 μM | <10 | <10 |
| Cells + STI-571 5 μM | <10 | <10 |
| Cells + STI-57I 10 μM | <10 | <10 |
| Cells + HIV-1 Bal + STI-571 1 μM | 287 +/− 31 | 744 +/− 27 |
| Cells + HIV-1 Bal + STI-571 5 μM | 212 +/− 44 | 556 +/− 28 |
| Cells + HIV-1 Bal + STI-571 10 μM | 127 +/− 22 | 245 +/− 31 |

Experiment 10

Development of Tyrosine Kinase Inhibitors

The present experiment was designed to develop new potent inhibitors for a number of biologically relevant tyrosine kinases (Abl, PDGFR, and Src). STI-571 and pyrido [2,3-d]pyrimidines were derivitized (Goosney et al. (2000) *Ann. Rev. Cell Dev. Biol.,* 16: 173; Knutton et al. (1989) *Lancet* 2: 218). These derivatives were screened on the basis of different desired characteristics, including optimization of solubility, mere pharmacokinetic and pharmacodynamic properties, as well as specificity in blocking kinases affecting microbial pathogenesis but not those affecting immune clearance. Based upon such screening, STI-571 was identified (see Experiment 2 above). These results demonstrate that derivatizing STI-571 and pyrido[2,3-d]pyrimidines can yield molecules with novel specificities or desirable in vivo properties.

Experiment 11

Effects of Tyrosine Kinase Inhibitors on Pathogenesis of TB In Vitro

The present experiment addressed whether selected tyrosine kinase inhibitors can affect pathogenesis of *Mycobacterium tuberculosis* (TB), the etiologic agent of tuberculosis. Invasion of TB into a cultured human macrophages (line THP-1) was carried out essentially as described in Miller and Shinnick (2001), *BMC Microbiol.,* 1: 26. Briefly, TB cultures was be added to the cells for between 30 minutes and two hours. Actinomycin D was then be added to the cultures to kill any bacteria remaining extracellularly. The actinomycin D was then washed away, and the cells lysed to release invaginated bacteria. The lysate was then be plated on bacterial plates, and the number of recovered colonies counted. The experiments were performed with or without addition of PD, STI-571 at concentrations ranging from 100 nM to 10 μM, concentrations that have proven effective in other EPEC and VV assays.

Figure 9:
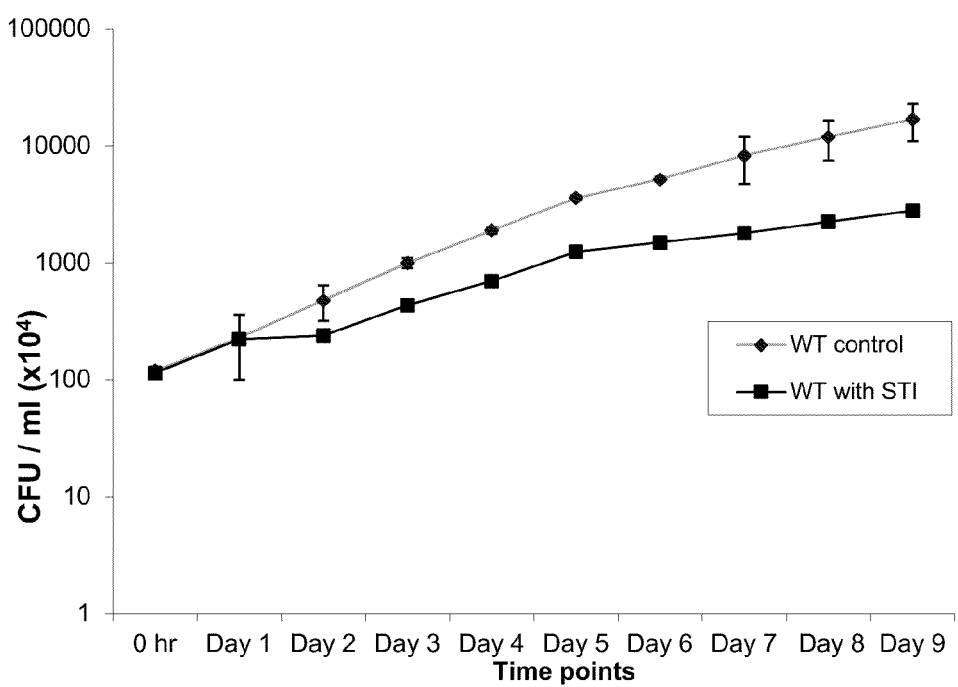
FIG. 9 shows the intercellular survival of *M. tuberculosis* after no exposure vs. exposure to STI-571 at various time points. WT stands for cells not exposed to any drug.

Colony counts were an indication of whether invasion was inhibited. Cell growth assays and trypan blue exclusion were used to verify that the macrophages were not adversely affected by the drugs. Results indicated that STI-571 increases the intercellular survival of *M. tuberculosis* (FIG. 9). These results indicate that tyrosine kinase inhibitors are effective in inhibiting TB infection.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. Further, it must be noted that as used in this specification and the appended embodiments, the singular forms "a," an" and "the" include plural referents unless the context clearly dictates otherwise.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

What is claimed is:

1. A method for treating a bacterial infection or a viral infection comprising administering a therapeutically effective amount of a tyrosine kinase inhibitor to a subject in need thereof, wherein said tyrosine kinase inhibitor comprises a compound according to the formula:

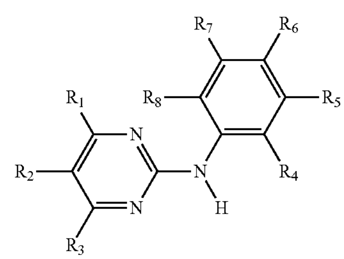

wherein:

$R_1$ is 4-pyrazinyl, 1-methyl-IH-pyrrolyl, amino-, or amino-lower alkyl-substituted phenyl wherein the amino group in each case is free, alkylated, or acylated, 1H-indolyl or 1H-imidazolyl bonded at a five-membered ring carbon atom, or unsubstituted or lower alkyl-substituted pyridyl bonded at a ring carbon atom and unsubstituted or substituted at the nitrogen atom by oxygen;

$R_2$ and $R_3$ are each independently of the other hydrogen or lower alkyl, one or two of the radicals $R_4$, $R_5$, $R_6$, $R_7$, and $R_8$ are each nitro, fluoro-substituted lower alkoxy or a radical of the formula $$—N(R_9)—C(=X)—(Y)_n—R_{10};$$

wherein:

$R_9$ is hydrogen or lower alkyl;

X is oxo, thio, imino, N-lower alkyl-imino, hydroximino, or O-lower alkyl-hydroximino;

Y is oxygen or the group NH, n is 0 or 1; and $R_{10}$ is an aliphatic radical having at least 5 carbon atoms, or an aromatic, aromatic-aliphatic, cycloaliphatic, cycloaliphatic-aliphatic, heterocyclic, or hetero-cyclicaliphatic radical;

and the remaining radicals $R_4$, $R_5$, $R_6$, $R_7$, and $R_8$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified, or esterified hydroxy, free, alkylated or acylated amino or free or esterified carboxy;

or a pharmaceutically acceptable salt, enantiomer, ester, amide, prodrug, or derivative thereof, or the metabolite structure

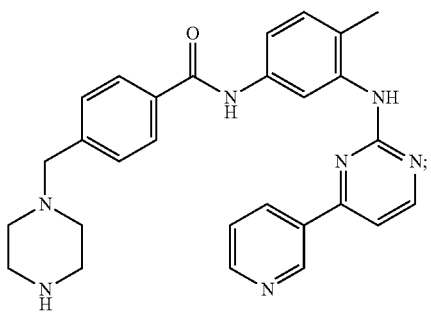 [SMILES: Cc1ccc(NC(=O)c2ccc(CN3CCNCC3)cc2)cc1Nc1nccc(-c2cccnc2)n1]

wherein said bacterial infection is caused by *Mycobacterium tuberculosis, Pseudomonas, Chlamydia, Helicobacter pylori, Listeria monocytogenes,* or *Shigella flexneri.*

2. The method according to claim 1, wherein said tyrosine kinase inhibitor comprises a compound according to the formula of claim 1 wherein:

$R_1$ is 4-pyrazinyl, 1-methyl-1H-pyrrolyl, amino-, or amino-lower alkyl-substituted phenyl wherein the amino group in each case is free, alkylated by one or two lower alkyl radicals or acylated by lower alkanoyl or by benzoyl, 1H-indolyl or 1H-imidazolyl bonded at a five-membered ring carbon atom, or unsubstituted or lower alkyl-substituted pyridyl bonded at a ring carbon atom and unsubstituted or substituted at the nitrogen atom by oxygen;

$R_2$ and $R_3$ are each independently of the other hydrogen or lower alkyl, one or two of the radicals $R_4$, $R_5$, $R_6$, $R_7$, and $R_8$ are each nitro, fluoro-substituted lower alkoxy or a radical of the formula

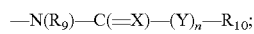

wherein:

$R_9$ is hydrogen or lower alkyl;
X is oxo, thio, imino, N-lower alkyl-imino, hydroximino, or O-lower alkyl-hydroximino;
Y is oxygen or the group NH;
n is 0 or 1; and
$R_{10}$ is an aliphatic hydrocarbon radical having 5-22 carbon atoms, a phenyl or naphthyl radical each of which is unsubstituted or substituted by cyano, lower alkyl, hydroxyl-lower alkyl, amino-lower alkyl, (4-methyl-piperazinyl)-lower alkyl, trifluoromethyl, hydroxy, lower alkoxy, lower alkanoyloxy, halogen, amino, lower alkylamino, di-lower alkylamino, lower alkanoylamino, benzolylamino, carboxy or by lower alkoxycarbonyl, or phenyl-lower alkyl wherein the phenyl radical is unsubstituted or substituted as indicated above, a cycloalkyl or cycloalkenyl radical having up to 30 carbon atoms, cycloalkyl-lower alkyl or cycloalkenyl-lower alkyl each having up to 30 carbon atoms in the cycloalkyl or cycloalkenyl moiety, a monocyclic radical having 5 or 6 ring members and 1-3 ring hetero atoms selected from nitrogen, oxygen, and sulfur, to which radical one or two benzene radicals may be fused, or lower alkyl substituted by such a monocyclic radical;

and the remaining radicals $R_4$, $R_5$, $R_6$, $R_7$, and $R_8$ are each independently of the others hydrogen, lower alkyl that is unsubstituted or substituted by amino, lower alkylamino, di-lower alkylamino, piperazinyl, piperidinyl, pyrrolidinyl, or by morpholinyl, or lower alkanoyl, trifluoromethyl, hydroxy, lower alkoxy, lower alkanoyloxy, halogen, amino, lower alkylamino, di-lower alkylamino, lower alkanoylamino, benzoylamino, carboxy, or lower alkoxycarbonyl;

or a pharmaceutically acceptable salt, enantiomer, ester, amide, prodrug, or derivative thereof, or metabolite structure

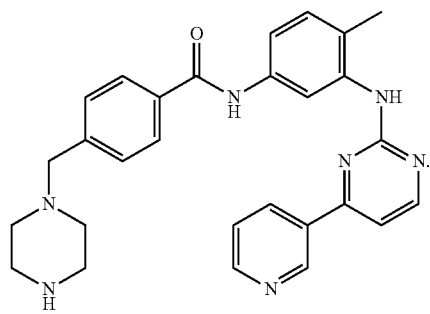 [SMILES: Cc1ccc(NC(=O)c2ccc(CN3CCNCC3)cc2)cc1Nc1nccc(-c2cccnc2)n1]

3. A method for treating a bacterial infection or a viral infection comprising administering a therapeutically effective amount of a tyrosine kinase inhibitor to a subject in need thereof, wherein said tyrosine kinase inhibitor comprises a compound according to the formula:

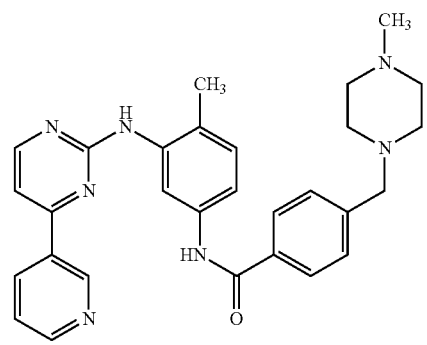 [SMILES: Cc1ccc(NC(=O)c2ccc(CN3CCN(C)CC3)cc2)cc1Nc1nccc(-c2cccnc2)n1]

or a pharmaceutically acceptable salt, enantiomer, ester, amide, prodrug, or derivative thereof, or metabolite structure

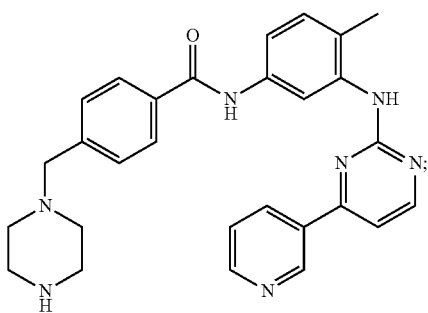 [SMILES: Cc1ccc(NC(=O)c2ccc(CN3CCNCC3)cc2)cc1Nc1nccc(-c2cccnc2)n1]

wherein said bacterial infection is caused by *Mycobacterium tuberculosis, Pseudomonas, Chlamydia, Helicobacter pylori, Listeria monocytogenes,* or *Shigella flexneri.*

4. The method according to claim 1, wherein said tyrosine kinase inhibitor comprises a derivative according to the formula:

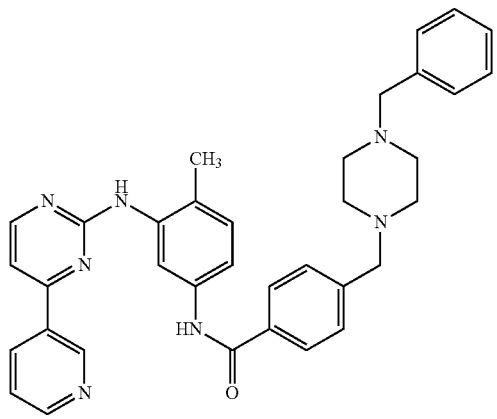 [SMILES: Cc1ccc(NC(=O)c2ccc(CN3CCN(Cc4ccccc4)CC3)cc2)cc1Nc1nccc(-c2cccnc2)n1]

or a pharmaceutically acceptable salt, enantiomer, ester, amide, prodrug, or derivative thereof, or metabolite structure

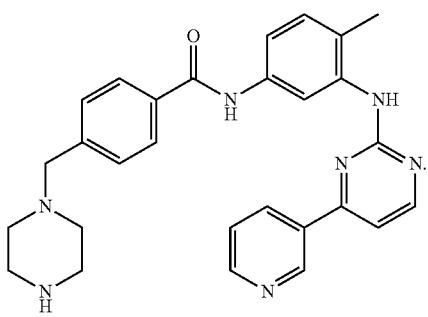 [SMILES: Cc1ccc(NC(=O)c2ccc(CN3CCNCC3)cc2)cc1Nc1nccc(-c2cccnc2)n1]

5. The method of claim 1, wherein the bacterial infection is caused by *Mycobacterium tuberculosis, Pseudomonas* or *Chlamydia,* and the viral infection is causes by a polyoma, HIV, Poxviridae, Orthomyxoviridae or Hepadnaviridae virus.

6. The method of claim 1, wherein said tyrosine kinase inhibitor inhibits viral replication.

7. The method of claim 1, wherein said tyrosine kinase inhibitor inhibits at least one Abl-family tyrosine kinase or Src-family tyrosine kinase.

8. The method of claim 7, wherein said Abl-family tyrosine kinase inhibitor is imatinib mesylate or a pharmaceutically acceptable salt, enantiomer, ester, amide, prodrug or derivative of imatinib mesylate, or the metabolite structure

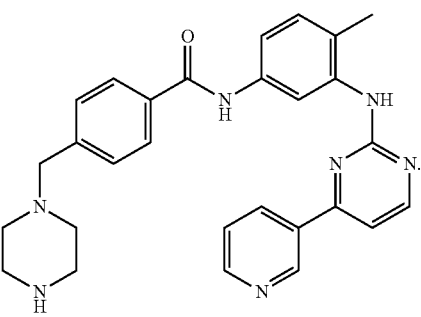 [SMILES: Cc1ccc(NC(=O)c2ccc(CN3CCNCC3)cc2)cc1Nc1nccc(-c2cccnc2)n1]

9. The method of claim 8, wherein said derivative of imatinib mesylate is STI-X.

10. The method of claim 1, wherein said tyrosine kinase inhibitor is administered orally, nasally, buccally, sublingually, intravenously, transmucosally, rectally, topically, transdermally, subcutaneously, by inhalation, or intrathecally.

11. The method of claim 1, wherein said viral infection is caused by a Vaccinia virus, a variola virus, a JC virus, a BK virus, a herpes virus, or a human immunodeficiency virus.

12. The method of claim 1, wherein said bacterial infection is caused by *Helicobacter pylori, Listeria monocytogenes, Shigella flexneri,* or *Mycobacterium tuberculosis.*

13. The method of claim 1, wherein said viral infection is caused by a Vaccinia virus, a variola virus, a polyoma virus, a Herpes virus, a cytomegalovirus (CMV), or a human immunodeficiency virus.

14. The method of claim 1, wherein said tyrosine kinase inhibitor is an Abl-family tyrosine kinase inhibitor.

15. The method of claim 14, wherein said Abl-family tyrosine kinase inhibitor is imatinib mesylate or STI-X.

16. The method of claim 3, wherein said bacterial infection is caused by *Helicobacter pylori, Listeria monocytogenes, Shigella flexneri,* or *Mycobacterium tuberculosis.*

17. The method of claim 16, wherein said tyrosine kinase inhibitor inhibits an Abl-family tyrosine kinase.

18. The method of claim 17, wherein said Abl-family tyrosine kinase inhibitor is imatinib mesylate or STI-X.

* * * * *

UNITED STATES PATENT AND TRADEMARK OFFICE
CERTIFICATE OF CORRECTION

PATENT NO. : 8,765,777 B2  
APPLICATION NO. : 12/969659  
DATED : July 1, 2014  
INVENTOR(S) : Daniel Kalman et al.

It is certified that error appears in the above-identified patent and that said Letters Patent is hereby corrected as shown below:

On the Title Page, under "Related U.S. Application Data" Item (63):

Continuation of application No. 12/774,828, filed on May 6, 2010, now abandoned, which is a continuation of application No. 12/551,871, filed on Sep. 1, 2009, now abandoned, which is a continuation of application No. 12/343,764, filed on Dec. 24, 2008, now abandoned.

Should read and be replaced as follows:

Continuation of application No. 12/774,828, filed on May 6, 2010, now abandoned, which is a continuation of application No. 12/551,871, filed on Sep. 1, 2009, now abandoned, which is a continuation of application No. 12/343,764, filed on Dec. 24, 2008, now abandoned, which is a continuation of application No. 10/586,382, filed on Jul. 19, 2006, now abandoned, which is a 371 of application No. PCT/US2005/001710, filed on Jan. 20, 2005, which claims benefit of application No. 60/537,960, filed Jan. 20, 2004, and claims benefit of application No. 60/553,681, filed Mar. 16, 2004, and claims benefit of application No. 60/614,203, filed Sep. 29, 2004.

Signed and Sealed this
Twenty-first Day of April, 2015

Michelle K. Lee
*Director of the United States Patent and Trademark Office*